US006441020B1

(12) United States Patent
Quick et al.

(10) Patent No.: US 6,441,020 B1
(45) Date of Patent: Aug. 27, 2002

(54) PROTEIN KINASE C MODULATORS. W.

(75) Inventors: James Quick, Lexington; Paul E. Driedger, Boston, both of MA (US)

(73) Assignee: Procyon Pharmaceuticals, Inc., Woburn, MA (US)

( * ) Notice: Subject to any disclaimer, the term of this patent is extended or adjusted under 35 U.S.C. 154(b) by 0 days.

(21) Appl. No.: 09/161,802

(22) Filed: Sep. 28, 1998

Related U.S. Application Data

(63) Continuation-in-part of application No. 08/549,135, filed on Oct. 27, 1995, now abandoned.
(51) Int. Cl.[7] .................... A61K 31/407; C07D 487/06; C07D 487/08
(52) U.S. Cl. .......................... 514/411; 514/63; 514/81; 514/185; 540/452; 540/460
(58) Field of Search ................. 540/452, 460; 514/411

(56) References Cited

U.S. PATENT DOCUMENTS

| | | | |
|---|---|---|---|
| 5,089,517 A | 2/1992 | Choi et al. | 514/411 |
| 5,145,842 A | 9/1992 | Driedger et al. | 514/63 |
| 5,292,765 A | 3/1994 | Choi et al. | 514/411 |
| 5,773,428 A | * 6/1998 | Castelhano et al. | 514/80 |

FOREIGN PATENT DOCUMENTS

| | | |
|---|---|---|
| WO | 87/07599 | 12/1987 |
| WO | 92/02484 | 2/1992 |

OTHER PUBLICATIONS

Irie et al. (Tennen Yuki Kagobutsu Toronaki Koen Yoshishu (1987), 29, 232–9).*
Hagiwara et al. (Agric. Biol. Chem. (1988), 52(3), 641–8).*
Irie et al. (Int. J. Cancer(1989), 43(3), 513–19).*
Irie et al. (Tetrahedron (1987), 43 (22), 5251–60.*
Irie et al. (Tetrahedron (1990), 46 (8), 2773–88).*
De Laszlo et al. (J. Chem., Soc., Chem. Commun. (1986), (4), 344–6).*
Koshimizu et al. (Tennen Yuki Kagobutsu Toronaki Koen Yoshishu (1985), 27th, 640–7).*
Sugimura, T., "Potent Tumor Promoters Other Than Phorbol Ester and Their Significance," *Gann* 73: 499–507 (1982).
Endo, Y. et al. "Synthesis of Optically Active Teleocidin Derivatives. Absolute Configuration of Teleocidin B and Olivoretin A," *Chem. Pharm. Bull.* 32: 358–361 (1984).
Horiuchi, T. et al., "Studies on Olivoretins Indicate a Requirement for a Free Hydroxyl Group for Teleocidin B Activity," *Gann* 75: 837–840 (1984).
Irie, K. et al., "Structure–Activity Relationship in the Induction of Epstein–Barr Virus by Teleocidin Derivatives," *Int. J. Cancer* 36: 485–488 (1985).
Irie, K. et al., "Epstein–Barr Virus Early Antigen Inducing Activity of 14–0–Derivatives of (–)–Indolactam V," *Agric. Biol. Chem.* 49(5): 1441–1446 (1985).
Fujiki, H. et al., "Structural–Activity Studies on Synthetic Analogues (Indolactams) of the Tumor Promoter Teleocidin," *Gann,* 75:866–870 (Oct. 1984).
Irie, K. and Koshimizu, K., "Structure–Activity Studies of Indole Alkaloid Tumor Promoters," *Mem. Coll. Agric. Kyoto Univ.,* 132: 1–59 (1988).
Endo, Y., "Synthesis of 7–Substituted Indolactam–V." *Tetrahedron* 43(10) :2241–2247 (1987).

* cited by examiner

*Primary Examiner*—Richard L. Raymond
(74) *Attorney, Agent, or Firm*—Hamilton, Brook, Smith & Reynolds, P.C.

(57) ABSTRACT

Compositions of matter having protein kinase C-modulatory, anti-inflammatory and other biological activities are disclosed. The compositions are derived from indolactams which have a substituent, containing at least one carbon, at the $N^1$ position and have ether substitution on the 14-O position.

20 Claims, No Drawings

PROTEIN KINASE C MODULATORS. W.

RELATED APPLICATION

This application is a continuation-in-part of application Ser. No. 08/549,135, filed Oct. 27, 1995, now abandoned, which is herein incorporated by reference in its entirety.

GOVERNMENT FUNDING

A portion of this invention was made with U.S. government support under grant number 1R43GM42285 from the National Institutes of Health (NIGMS). The government may have certain rights in this invention.

BACKGROUND

Protein kinase C (also known as "calcium/phospholipid-dependent protein kinase", "PKC" or "C-kinase) is a family of very closely related enzymes; one or more members of the protein kinase C family are found in nearly all animal tissues and animal cells that have been examined. The identity of protein kinase C is generally established by its ability to phosphorylate certain proteins when adenosine triphosphate and phospholipid cofactors are present, with greatly reduced activity when these cofactors are absent. Protein kinase C is believed to phosphorylate only serine and/or threonine residues in the proteins that are substrates for protein kinase C. Additionally, some forms of protein kinase C require the presence of calcium ions for maximal activity.

Protein kinase C activity is also substantially stimulated by certain 1,2-sn-diacylglycerols that bind specifically and stoichiometrically to a recognition site or sites on the enzyme. This site is called the diacylglycerol binding site, and it is located on the amino-terminal portion of protein kinase C, the so-called "regulatory domain". The carboxy-terminal portion of protein kinase C carries the site at which protein phosphorylation is effected, and this portion is thus called the "kinase domain".

Thus, the rate at which various protein kinase C family members carry out their enzymatic phosphorylation of certain substrates can be markedly enhanced by the presence of the cofactors such as phospholipids, diacylglycerols and, for some protein kinase C family members, calcium ions. This stimulation of protein kinase C activity is referred to as protein kinase C "activation", and the activation of protein kinase C by the binding of diacylglycerols to the regulatory domain of protein kinase C is of particular importance in the normal and pathological functions of protein kinase C.

In contrast to the activation of protein kinase C, some chemical compounds have been shown, when added to protein kinase C enzyme assays, to reduce the rate at which protein kinase C phosphorylates its substrates; such compounds are referred to as protein kinase C "inhibitors" or, in some cases, "antagonists". In some circumstances, protein kinase C inhibitors are capable of inhibiting various cellular or tissue phenomena which are thought to be mediated by protein kinase C.

Activation of protein kinase C by diacylglycerols has been shown to be an important physiological event that mediates the actions of a wide variety of hormones, neurotransmitters, and other biological control factors such as histamine, vasopressin, α-adrenergic agonists, dopamine agonists, muscarinic cholinergic agonists, platelet activating factor, etc. {see Y. Nishizuka, *Nature* 308: 693–698 (1984) and *Science* 225: 1365–1370 (1984) for reviews}.

The biological role of protein kinase C is also of great interest because of the discovery that certain very powerful tumor promoting chemicals activate this enzyme by binding specifically and with very high affinity to the diacylglycerol binding site on the enzyme. In addition to diacylglycerols, there are at present six other known classes of compounds that bind to this site: diterpenes such as the phorbol esters; indole alkaloids (indolactams) such as the teleocidins, lyngbyatoxin, and indolactam V; polyacetates such as the aplysiatoxins and oscillatoxins; certain derivatives of diaminobenzyl alcohol; macrocyclic lactones of the bryostatin class; and benzolactams such as (−)-BL-V8-310. The phorbol esters have long been known as powerful tumor promoters, the teleocidins and aplysiatoxins are now known to have this activity, and it appears likely that additional classes of compounds will be found to have the toxic and tumor promoting activities associated with the capability to bind to the diacylglycerol site of protein kinase C and thus activate the enzyme. Other toxicities of these agents when administered to animals include lung injury and profound changes in blood elements, such as leukopenia and neutropenia.

Representative examples of these seven classes of previously known protein kinase C-activating compounds, collectively referred to herein as "phorboids", are depicted below:

TYPICAL DITERPENE-TYPE PHORBOID AGONISTS

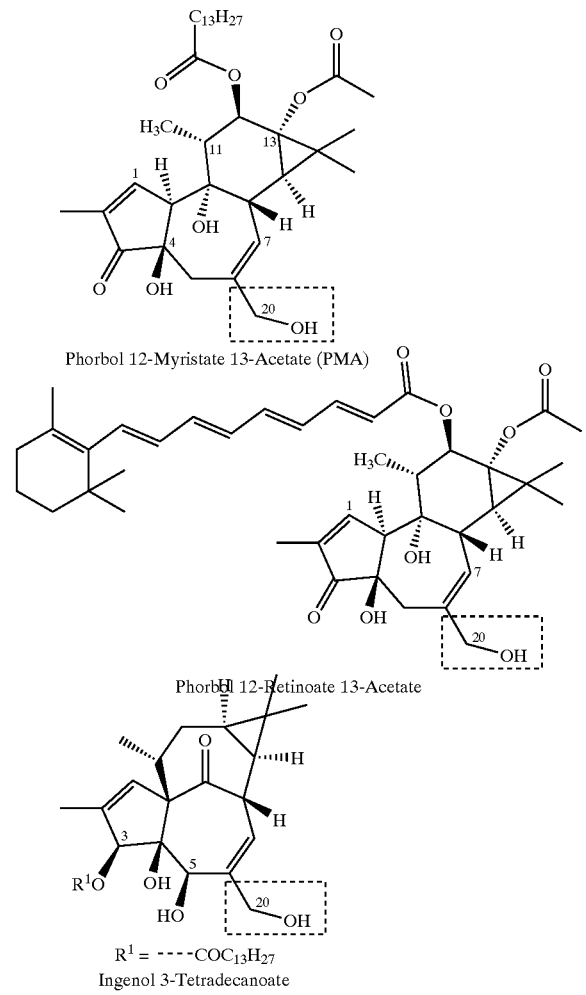

Phorbol 12-Myristate 13-Acetate (PMA)

Phorbol 12-Retinoate 13-Acetate $R^1 = \text{----COC}_{13}H_{27}$
Ingenol 3-Tetradecanoate

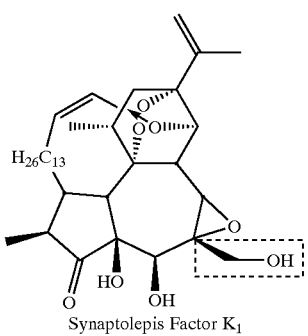
Synaptolepis Factor K₁
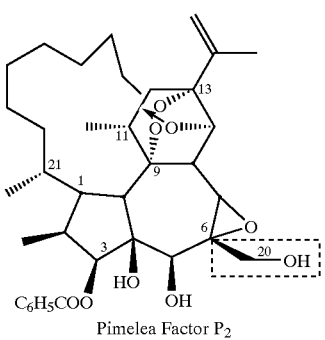
Pimelea Factor P₂
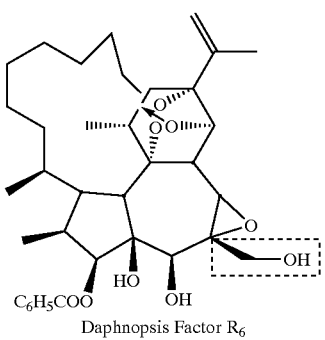
Daphnopsis Factor R₆
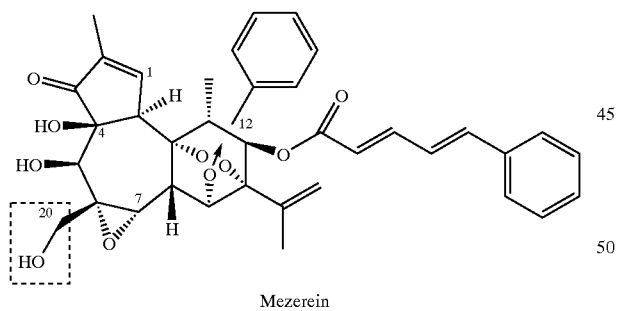
Mezerein
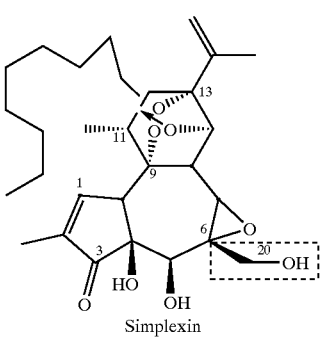
Simplexin
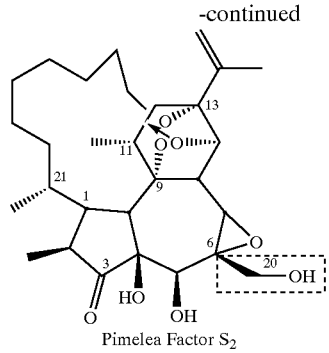
Pimelea Factor S₂
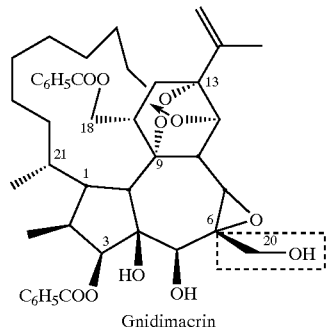
Gnidimacrin
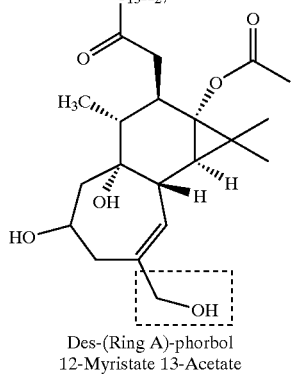
Des-(Ring A)-phorbol
12-Myristate 13-Acetate
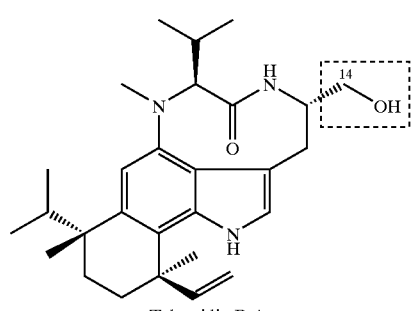
Teleocidin B-4
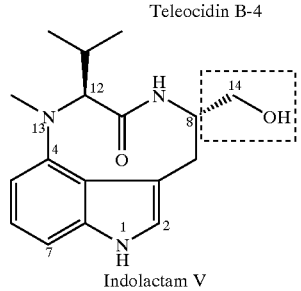
Indolactam V

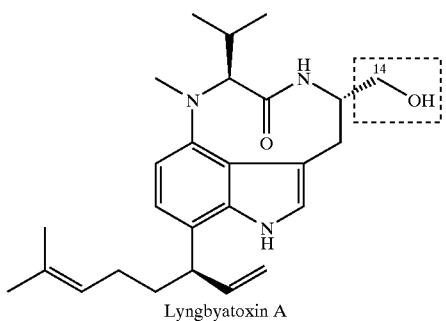
Lyngbyatoxin A
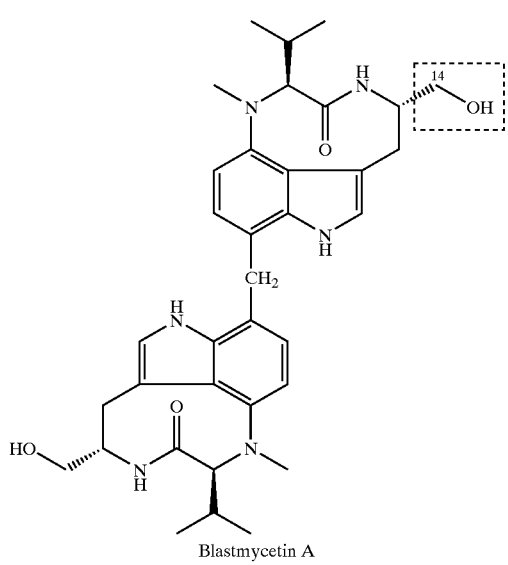
Blastmycetin A
TYPICAL DIACYLGLYCEROL-TYPE PHORBOID AGONISTS
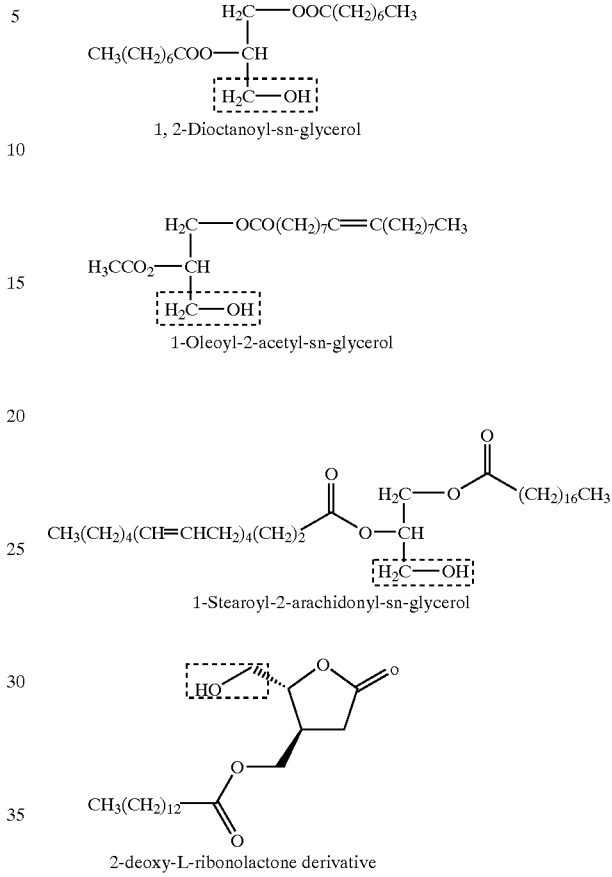
1, 2-Dioctanoyl-sn-glycerol
1-Oleoyl-2-acetyl-sn-glycerol
1-Stearoyl-2-arachidonyl-sn-glycerol
2-deoxy-L-ribonolactone derivative
TYPICAL DIAMINOBENZYL ALCOHOL-TYPE PHORBOID AGONISTS
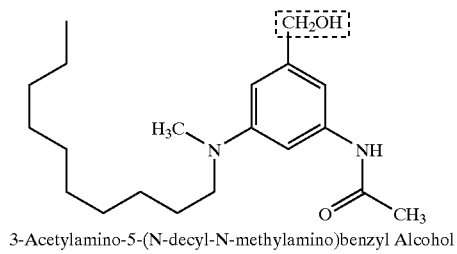
3-Acetylamino-5-(N-decyl-N-methylamino)benzyl Alcohol
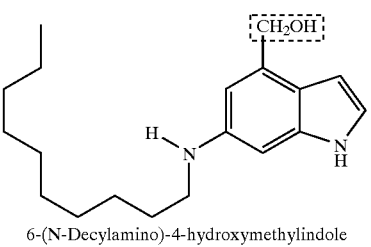
6-(N-Decylamino)-4-hydroxymethylindole 4-hydroxymethyl-
4-tetradecanoyloxymethyl-
4-butanolide 3-hydroxymethyl-1, 6-dioxo-
2, 5-dioxacyclocosane

TYPICAL POLYACETATE-TYPE PHORBOID AGONISTS

Aplysiatoxin and its debromo, bromo and dibromo derivatives

R's = H or Br

TYPICAL BRYOSTATIN-TYPE PHORBOID AGONISTS

Bryostatin 1

Bryostatin 2

TYPICAL BENZOLACTAM-TYPE PHORBOID AGONISTS (−)-BL-V8-310

(+)-epi-BL-V8-310 racemic epi-BL-V9-310

It can be seen that the seven basic classes of phorboids depicted have, from one class to another, diverse structural elements of both hydrophilic and hydrophobic nature, with one prominent exception, namely that each contains a hydroxymethyl or 1-hydroxyethyl group (indicated by the dashed-line boxes in each structure). In each case the phorboid depicted is among the most potent of its particular structural class, and among the seven classes the diterpenes, indolactams, polyacetates, bryostatins and benzolactams have members of especially high potency.

In addition to potent tumor promoting activity, these seven classes of compounds display a vast range of biological activities, as would be expected from the widespread distribution of their target enzyme. Some of these activities, like tumor promotion, indicate the involvement of protein kinase C in important normal or pathological processes in animals. Thus, the phorboids are potent skin inflammatory agents, cause smooth muscle contraction in several tissues, alter immune system function and can be used to cause a variety of other normal or pathological responses. Related disease states such as the development of cancer, the onset and/or maintenance of inflammatory disease, the role of vasoconstriction in hypertension, the role of bronchoconstriction in asthma, the life cycles of many pathogenic human viruses, and the role of cholinergic, adrenergic, and dopaminergic synapses in diseases of the central/peripheral nervous systems, may be mediated in vivo by the stimulation of protein kinase C or other diacylglycerol binding site-bearing entities by diacylglycerols, the latter being generated in the cell by pathological agents or conditions.

In analyzing the activity of a pharmaceutical or other bioactive compound, it is useful to consider two properties: the efficacy, defined as the capability to elicit a full or partial biological result, such as complete displacement of a ligand from its receptor site or the complete inhibition of inflammation or edema caused by a standard stimulus; and the potency, defined as that amount or concentration of drug that causes 50% of the full response (often abbreviated as the $ED_{50}$). It is frequently the case within a given class of pharmaceutical agents that individual members of the class all have equal efficacy, i.e. they each can generate a full biological effect, but they show differing potencies. Thus, the structural modifications within such a class affect only the amount necessary to achieve a given result, and the modified compounds otherwise have generally the same central biological characteristic. There may also be differences between members of such a class as regards properties other than the central biological characteristic; for example, members of the class might differ in side effects or toxicity.

Well-known pharmaceuticals that have been in extensive use for years or decades show a wide range of optimal therapeutic potencies. Aspirin, for example, is often taken in multi-gram amounts per day for treatment of inflammation or arthritis, and detailed analyses of its mechanism of action in vitro show that a concentration in the millimolar range is required. In contrast, steroid-based, topical anti-inflammatory compounds, such as fluocinolone acetonide, are many thousand-fold more potent, and, beyond this, some oral contraceptive agents are prescribed in daily doses in the microgram range. Thus, although high potency is generally advantageous for a pharmaceutical, it is not an absolute requirement.

A thousand or more analogs of the highly skin-inflammatory and tumor-promoting phorboids have been reported in the literature, including numerous examples on which minor chemical modifications have been made {see Evans and Soper, *Lloydia* 41: 193–233 (1978) and references cited therein}. The structures of these phorboids can be compared, and their activities for inflammation and tumor promotion can be analyzed from the perspective of efficacy and potency. The structures of the different classes of phorboids vary quite markedly from one to the other class, yet widespread testing of their biological activities has shown that the members of these classes known prior to P. E. Driedger and J. Quick, U.S. Pat. No. 5,145,842 (Sep. 8, 1992) have generally very similar biological properties. In particular, the numerous previously known phorboids of the highly potent diterpene, indolactam, and polyacetate classes appear to have, with very minor exceptions, virtually identical efficacies as skin irritants and tumor promoters {T. Sugimura, *Gann* 73: 499–507 (1982)}. The exceptions involve a few compounds that have a short duration of irritant activity and/or manifest diminished tumor promoting activity, perhaps due to toxicity or secondary parameters such as differing metabolic destruction rates.

In contrast to the essentially equal efficacies among the vast majority of previously known phorboids, their relative potencies cover a wide range, as measured in inflammation and promotion tests and as measured in numerous other in vivo and in vitro systems. Example compounds can be found in the diterpene, indolactam, and polyacetate classes that have nearly equal, very high potencies. At the same time there are compounds in each of these classes which embody significant structural changes that do not diminish efficacy but do result in potency decreases of 10-fold to 100,000-fold or more {see, for example, Driedger and Blumberg, *Cancer Res*. 37: 3257–3265 (1977), *Cancer Res*. 39: 714–719 (1979)}. Thus, all these compounds appear to be capable of achieving generally the same biological results, and merely differ in the amount which must be used to obtain a given result.

In vitro measurements of biochemical properties provide an even more sensitive method for comparing the properties of the various phorboids. For example, using a radioactively labeled phorboid such as [$^3$H]phorbol 12,13-dibutyrate or [$^3$H]lyngbyatoxin, one can measure the potency of a test compound as a competitive ligand for the diacylglycerol binding site, which is also referred to herein as the "phorboid binding site" on protein kinase C or on other biological molecules which have phorboid binding sites (see below). Alternatively, one can measure the ability of a given phorboid to stimulate the protein kinase C-mediated incorporation of radioactive phosphate from [$^{32}$P]adenosine triphosphate into a standard acceptor substrate such as histone H1. Tests of this nature reveal a difference in potency between given phorboid agonists of as much as 10,000,000-fold or more {Dunn and Blumberg, *Cancer Res*. 43: 4632–4637 (1983), Table 1}.

These basic data regarding the phorboid agonists are an important consideration because they underscore the concept that the structural differences among these previously known phorboids, especially the diterpenes, indolactams, polyacetates, and bryostatins, generally do not affect their efficacies as toxic agonists, and indeed a wide variety of structural changes are tolerated in this regard. Such changes generally alter potency only and do not provide agents with therapeutic utility, since the resulting compounds retain their toxicity.

Some minor changes in phorboid structure are known to result in generally inactive compounds, such as a stereochemical change from 4-β to 4-α in the phorbol series, and indeed some of the diterpene skeleton structures carry hydroxy groups that must be esterified in order for inflammatory activity to be observed. However, these inactive compounds are quite few in number among the known phorboids, and no therapeutic utility has been demonstrated for them.

The phorbol esters, indolactams, polyacetates, diaminobenzyl alcohols, and bryostatins are generally found in plants, molds, and algae, or are synthetic in origin. Although they are found in many parts of the world, normal human contact with them is thought to be low. In contrast, the diacylglycerols are part of the functioning of virtually every type of animal cell and, thus, the undesirable activation of protein kinase C by the diacylglycerols may have a very widespread role in human diseases.

Thus, compounds capable of blocking the activation of, or inhibiting, protein kinase C by acting as specific pharmacological antagonists of the diacylglycerols at the diacylglycerol binding site on protein kinase C, would be valuable agents in the prevention and treatment of a wide variety of diseases in animals and humans. For example, the need for, and potential utility of, protein kinase C inhibitors/antagonists as agents for the treatment of cancer has received much attention {D. Corda, et al., *Trends in Pharmacological Sciences* 11: 471–473 (1990); G. Powis, *Trends in Pharmacological Sciences* 12: 188–194 (1991); S. Gandy and P. Greengard, *Trends in Pharmacological Sciences* 13: 108–113 (1992); B. Henderson and S. Blake, *Trends in Pharmacological Sciences* 13: 145–152 (1992)}.

Protein kinase C comprises a family of eleven or more closely related protein molecules, designated by the lower-case Greek letters α, β1, β2, γ, δ, ε, ζ, η, θ, ι (also known as λ) and μ. Because of their high degree of relatedness they are referred to as "isozymes", "isotypes" or "isoforms". Occasionally the term "subtypes" is used, but this term is usually reserved to designate, as a subdivision, two or more variants of a single isotype.

The currently known isotypes of protein kinase C have all been characterized in molecular detail by numerous laboratories, and are subdivided into several subfamilies: α, β1, β2 and γ (the "A-group"); δ, ε, ε', {Ono, Y. et al., *J. Biol. Chem.* 263: 6927–6932 (1988)}, η {also known as protein kinase C-L; Osada, S. et al., *J. Biol. Chem.* 265: 22434–22440 (1990) and Bacher, N. et al, *Mol. Cell. Biol.* 11: 126–133 (1991), respectively}, and θ {Osada, S.-I. et al., *Mol. Cell. Biol.* 12: 3930–3938 (1992) and Chang, J. D. et al., *J. Biol. Chem.* 268: 14208–14214 (1993)} (the "B-group"); ζ {Ono, Y. et al., *J. Biol. Chem.* 263: 6927–6932 (1988)} and ι {Selbie, L. A. et al., *J. Biol. Chem.* 268: 24296–24302 (1993)}, the latter also being known as PKCλ {Akimoto, K. et al., *J. Biol. Chem.* 269: 12677–12683 (1994)} (the "C-group"); and μ {Johannes, F.-J. et al., *J. Biol. Chem.* 269: 6140–6148 (1994)}, also known as PKD {Valverde, A. M. et al., *Proc. Natl. Acad. Sci. USA* 91: 8572–8576 (1994)} (the "D-group"). Members of the A-group require calcium ions for maximal activation, whereas the B-, C- and D-group members are thought to be largely calcium-independent for activation. The genes for each of the isotypes above have been cloned from one or more animal and yeast species and the clones have been sequenced; the relatedness of the genes and their product polypeptides is thus well established.

It is possible that the different protein kinase C isozymes have different biological roles, and published evidence supports this idea {Homan, E., Jensen, D. and Sando, J., *J. Biol. Chem.* 266: 5676–5681 (1991); Gusovsky, F. and Gutkind, S., *Mol. Pharm.* 39: 124–129 (1991); Borner, C., "The role of protein kinase C in growth control", Sixth International Symposium on Cellular Endocrinology, W. Alton Jones Cell Science Center, Lake Placid, N.Y., August 12–15, 1990; Naor, Z. et al., *Proc. Natl. Acad. Sci. USA* 86: 4501–4504 (1989); Godson, C., Weiss, B. and Insel, P., *J. Biol. Chem.* 265: 8369–8372 (1990); Melloni, E. et al., *Proc. Natl. Acad. Sci. USA* 87: 4417–4420 (1990); Koretzky, G. et al., *J. Immunology* 143: 1692–1695 (1989)}. For example, the stimulation of one protein kinase C isotype or a limited subset of protein kinase C isotypes might lead to undesirable results such as the development of inflammation {Ohuchi, K. et al., *Biochim. Biophys. Acta* 925: 156–163 (1987)}, the promotion of tumor formation {Slaga, T., *Envir. Health Perspec.* 50: 3–14 (1983)} or an increased rate of viral replication in cells (i.e., de novo infection of cells and/or expression, assembly and release of new viral particles) {Harada, S. et al., *Virology* 154: 249–258 (1986)}.

On the other hand, other protein kinase C isozymes might be responsible for the many beneficial effects observed when protein kinase C is stimulated by known protein kinase C activators in a variety of biological settings; such beneficial effects include the cessation of division of leukemic cells {Rovera, G., O'Brien, T. and Diamond, L., *Science* 204: 868–870 (1979)}, multiplication of colonies of lymphocytes {Rosenstreich, D. and Mizel, S., *J. Immunol.* 123: 1749–1754 (1979)} and leucocytes {Skinnider, L. and McAskill, J., *Exp. Hematol.* 8: 477–483 (1980)}, increase in production of soluble Alzheimer precursor protein and reduction in production of the Aβ peptide characteristic of Alzheimer's Disease {Demaerschalk, I. et al. *Biochim. Biophys. Acta* 1181: 214–218 (1993); Buxbaum, J. D. et al. *Proc. Acad. Sci. USA* 90: 9195–9198 (1993)} or the secretion of useful bioregulatory factors such as interferon-γ {Braude, I., U.S. Pat. No. 4,376,822} and interleukin-2 {Gillis, S., U.S. Pat. No. 4,401,756}.

Recent publications indicate that diacylglycerol binding sites exist on newly-described proteins which lack the kinase domain, and, thus, lack the kinase activity, of protein kinase C. One such protein is n-chimaerin, found in human brain {Ahmed et al., *Biochem. J.* 272: 767–773 (1990)}. Another group of such proteins comprises the unc-13 gene product of the nematode *Caenorhabditis elegans* {Maruyama, I. and Brenner, S., *Proc. Natl. Acad. Sci. USA* 88: 5729–5733 (1991)} and three mammalian homologs, Munc13-1, -2 and -3 {Brose, N. et al. *J. Biol. Chem.* 270: 25273–25280 (1995)}. The presence of the diacylglycerol binding sites on these two proteins was demonstrated by standard binding experiments with [$^3$H]phorbol 12,13-dibutyrate. These new proteins may have other, non-kinase enzymatic or biological activities which can be modulated by compounds which bind to their diacylglycerol binding sites. Thus, such compounds may have utility on non-protein kinase C biological targets.

Given that there are now numerous distinct biological entities bearing diacylglycerol binding sites, it would be highly desirable to obtain chemical compounds which could specifically and selectively target one or another type of diacylglycerol binding site, thus permitting one to selectively activate or inhibit one such site without affecting the others. Such compounds would be valuable experimental tools for studying the role of individual types of proteins bearing diacylglycerol binding sites as well as providing novel means for treating diseases in which protein kinase C or other diacylglycerol binding site-bearing proteins are involved.

There are several published reports describing chemical compounds capable of selectively distinguishing several diacylglycerol/phorboid-type binding sites in mouse skin {Dunn and Blumberg, op. cit.} and in purified preparations of protein kinase C isotypes {Ryves, W. J., et al., *FEBS Letters* 288: 5–9 (1991)}. However, in these studies, even the compounds showing the clearest differences in affinity for these distinct classes, namely phorbol 12,13-dibutyrate, 12-deoxyphorbol 13-isobutyrate, 12-deoxyphorbol 13-phenylacetate and thymeleatoxin, are only selective by a factor of 10–1000 in dissociation constant among the different binding sites. Furthermore, these compounds have potent skin inflammatory activity and are not desirable in human or animal medicine because of this and related toxicities.

Thus, to briefly recapitulate, two kinds of new compounds relating to diacylglycerol binding sites would be highly desirable. The first type would be capable of selectively activating one or a few useful, but not other, deleterious, diacylglycerol target sites. The second type would be capable of inhibiting, or antagonizing the stimulation of, one or more deleterious diacylglycerol binding site-bearing entities without blocking the useful ones, or would be capable of causing the loss from cells of PKC isotypes with deleterious properties but not loss of PKC isotypes with desirable properties. These kinds of compounds would be valuable agents for the study of diacylglycerol binding site-bearing entities and for the prevention or treatment of a wide range of human and animal diseases thought to involve protein kinase C or other entities under the control of diacylglycerol binding sites.

With the exception of recently reported modifications of the hydroxymethyl group {P. E. Driedger and J. Quick, U.S. Pat. No. 5,145,842 (Sept. 8, 1992), U.S. Pat. No. 5,643,948 (Jul. 1, 1997), U.S. Pat. No. 5,716,968 (Feb. 10, 1998) and U.S. Pat. No. 5,750,568 (May 12, 1998)}, earlier efforts to use the previously known phorboids themselves or to modify the structures of these known phorboids have generally not been successful in producing useful compounds with inflammatory toxicity low enough to consider use in humans.

It has been known for some time that several of the toxic, inflammatory and tumor-promoting compounds such as phorbol 12-tigliate 13-decanoate, mezerein, lyngbyatoxin and aplysiatoxin have anti-leukemic activity in mouse model tests {T. Sugimura, op cit.; S. M. Kupchan and R. L. Baxter, *Science* 187: 652–653 (1975); S. M. Kupchan, et al., *Science* 191: 571–572 (1976); M. C. Territo and H. P. Koeffler, *Br. J. Haematol.* 47, 479–483 (1981)}. However, these compounds are all extremely toxic and are cancer suspect agents, thus eliminating them from consideration as human therapeutic agents.

Ganong, et al. {*Proc. Nat. Acad. Sci. USA* 83: 1184–1188 (1986)} tested a series of diacylglycerols and found no antagonistic activity in that series against the standard agonist, 1,2-dioctanoylglycerol. It is of particular note that several compounds tested in this work were modified in the hydroxymethyl portion of the diacylglycerol molecule, and these modifications produced only a loss of activity or a weakened activity that was not distinguishable from the agonist activity of 1,2-dioctanoylglycerol itself, a compound which is toxic to mouse skin {R. Smart, et al., *Carcinogenesis* 7: 1865–1870 (1986); A. Verma, *Cancer Res.* 48: 2168–2173 (1988)}. These hydroxymethyl-modified compounds were not antagonists in these tests and no utility was found. Similarly, Thielmann and Hecker {*Forsch. Krebsforsch.* Vol. VII, pp. 171–179 (1969), New York: Schattauer} found only a complete loss of biological activity in their study when the hydroxy group of the hydroxymethyl on phorbol 12,13-didecanoate was replaced with hydrogen or chlorine. Schmidt and Hecker {H. Lettre and G. Wagner (eds.), *Aktuelle Probleme aus dem Gebiet der Cancerologie*, Vol. III, 3rd Heidelberg Symposium, pp. 98–108. Berlin: Springer Verlag, 1971 } also found that oxidation of the hydroxymethyl of phorbol 12,13-didecanoate to a carboxylic acid caused complete loss of activity in the assays used.

The hydroxymethyl group of the known phorboids (see structures above) has been thought to be required for biological activity, as detailed by Hecker (Hecker, E., *Carcinogenesis*, Vol. 2, eds. Slaga, Sivak and Boutwell, Raven Press, New York, 1978, pp. 11–48 and references cited therein). Indeed, it is stated therein that the replacement of the 20-hydroxyl in a phorbol ester "results in complete loss of biological activity". In another study, replacement of the hydroxy group of the hydroxymethyl (located at carbon 14) by chlorine or hydrogen in indolactam V gave rise to compounds with agonist activity weaker, than but otherwise not distinguished from, the agonist activity of the very toxic teleocidin class of tumor promoters {Irie et al., *Int. J. Cancer* 36: 485–488 (1985)}. Thus, no utility beyond that of the toxic, hydroxymethyl-bearing parent indolactam-type compounds was found.

Schmidt and Hecker (*Carcinogenesis*, Vol. 7, ed. by E. Hecker et al., Raven Press, New York, 1982, pp. 57–63) studied the abilities of a series of diterpene phorboids to inhibit tumor promotion by the standard phorboid agonist tumor promoter phorbol 12-myristate 13-acetate (PMA). They found that, at low doses, some short-chain ester derivatives of phorbol were able to block the tumor promotion by PMA. However, all of the compounds that were active as antagonists at low doses are also very efficacious skin irritants themselves at slightly higher doses and most of them are also known to have tumor promoting activity. Thus, these short-chain esters still have toxic inflammatory and tumor promoting activity at doses only slightly different from those which would be needed to exhibit a therapeutic effect in mice.

Irie and Koshimizu prepared $(-)-N^1,14-O-$dimethylindolactam V and $(-)-N^1,N^{10},14-O-$trimethylindolactam V by treatment of (−)-indolactam V with methyl p-toluenesulfonate in the presence of sodium hydride {Irie, K., and K. Koshimizu. "Structure-activity studies of indole alkaloid tumor promoters." *Mem. Coll. Agric., Kyoto Univ.* 132: 1–59 (1988)}. There was no report of evaluation of these compounds in a bioassay. In the same study (−)-14-O-methylindolactam V, (−)-14-O-butylindolactam V and (−)-O-hexylindolactam V were prepared and no induction of the Epstein-Barr virus early antigen in Raji cells could be detected. Furthermore, (−)-14-O-methylindolactam V did not measurably inhibit the binding of [$^3$H]PMA to a protein kinase C preparation. In contrast, (−)-indolactam V was very active in both assays.

Furthermore, Horiuchi and coworkers found that 14-O-methylteleocidins were inactive in a variety of biological assays including the inhibition of the binding of [$^3$H]PMA to a protein kinase C preparation {Horiuchi, T. et al. *Gann* 75: 837–840 (1984)}. As expected, the 14-hydroxy-containing teleocidins were active in those same assays.

Driedger and Quick, op cit., found that indolactam derivatives and analogs modified at the hydroxymethyl group with certain functional groups including carbamates had useful protein kinase C modulating activities including anti-inflammatory activities and were without the pro-inflammatory effects of the parent indolactams.

SUMMARY OF THE INVENTION

This invention pertains to novel phorboid derivatives of the indolactam class which variously block the toxic effects of the hydroxymethyl-containing phorboids, generally lack the toxic properties of previously available phorboids, show activity for applications as therapeutics and demonstrate the ability to selectively bind to and modulate certain protein kinase C isotypes at much higher potencies than for other protein kinase C isotypes. The phorboid derivatives of the present invention have utility as anti-inflammatory and anti-psoriatic agents, as cancer cell and leukemic cell inhibitory agents, anti-asthmatic and anti-hypertensive agents, as modulators of human immune cell function, as anti-viral agents, as stimulators of the production of lymphokines such as interferon and the interleukins, as central nervous system pharmaceuticals for several pathological conditions including Alzheimer's disease.

The structural features associated with the non-toxicity and diacylglycerol binding site modulating properties of these compounds relate primarily to the hydroxymethyl or 1-hydroxyethyl group found attached to carbon 9 of the parent indolactam compounds and to the substituent on the nitrogen 1 ($N^1$) of the indole ring. Specific modifications of these two sites of the indolactam molecule yield non-skin inflammatory compounds that show anti-inflammatory and other useful activity, whereas any of a very wide variety of changes in other parts of the parent indolactam phorboid structure have very markedly less effect on the overall biological properties of the derivatives, other than changes in potency. This invention also provides new compounds that discriminate between phorboid receptor-type targets with measured relative binding activities differing by 10–20 fold and with higher relative selectivities inferred from their binding versus non-inflammatory and anti-inflammatory activities.

The hydroxymethyl group found in the indolactam nucleus is a primary focus of this invention, in which the variations which can be accommodated in the organic functional groups replacing the hydroxymethyl/1-hydroxyethyl groups are found to include a wide variety of ethers. Furthermore, the parent indolactam structure has now also been found to yield compounds of particular protein kinase C isotype selectivity when $N^1$ carries groups other than hydrogen.

Generally, the indolactam derivatives of this invention can be represented by the formula:

wherein $P_I$ and $G_x$ are as defined below.

DETAILED DESCRIPTION OF THE INVENTION

The design of the phorboid derivatives of this invention is based on the finding that the indolactam hydroxymethyl group may be converted to any of a very wide variety of ethers, in conjunction with simultaneous replacement of the hydrogen on $N^1$ with an extremely broad range of organic substituents, with the result that the compounds so substituted have particularly favorable patterns of protein kinase C isotype selectivity, a lack of inflammatory activity and useful residual biological activities, such as anti-inflammatory properties. It is particularly surprising that the simultaneous presence, in the indolactam nucleus, of the substituents on $N^1$ and 14-O described in this invention leads to compounds of marked selectivity for protein kinase C isotypes of the A-group over protein kinase C isotypes of the B-group and having marked anti-inflammatory and other useful properties.

The compounds resulting from the hydroxymethyl and $N^1$ hydrogen replacements described here, variously, block the toxic effects of the hydroxymethyl-containing phorboids, lack the skin-inflammatory properties associated with the previously available phorboids, show useful activity as therapeutic agents and display the ability to distinguish between various protein kinase C isotypes. These new compounds have utility as, variously, anti-inflammatory agents, anti-viral agents and anti-leukemic agents, for example.

The compounds of the present invention provide significant improvement over previously known, related compounds. For example, 14-O-alkylindolactams which have a hydrogen at $N^1$ have been prepared by Irie and Koshimizu, op. cit., and, as noted above, have been found to be inactive in a variety of biological assays. It has now been determined that representative compounds of that class do not bind, except possibly at very high concentrations, to any of the known protein kinase C isotypes having functional diacylglycerol (DAG) binding sites, under conditions in which compounds of the present invention demonstrate good binding potency to DAG sites as well as marked selectivity for certain isotypes (see Example 23).

Furthermore, $N^1$-alkylindolactams, with the 9-hydroxymethyl in place, have also been prepared (Irie and Koshimizu, op. cit.). However, these latter compounds are potent inflammatory agents and, thus, have little, if any, therapeutic value for the utilities listed above for the compounds of the present invention.

The indolactam derivatives of this invention are represented as follows:

wherein $P_I$ and $G_x$ are as defined below.
$P_I$ is a moiety of the formula:

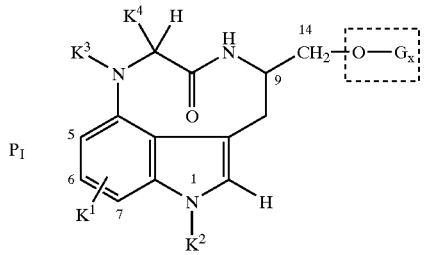

in the form of an individual isomer, an isomer mixture, a racemate or optical antipode, or a pharmaceutically acceptable salt thereof, wherein $K^1$ represents 1–3 sub stituents located independently at any of carbons 5, 6 and 7, which sub stituents are independently selected from the group consisting of hydrogen, halogen and a straight chain or branched chain, cyclic or acyclic, saturated or unsaturated or aromatic carbon- and/or heteroatom-containing moiety which moieties, taken together, contain not more than 40 carbon atoms, not more than 24 halogen atoms and not more than 9 heteroatoms selected from the group consisting of oxygen, nitrogen, silicon, phosphorus, and sulfur, the moieties being optionally connected to one another, to $K^3$ and/or to $K^2$ to form 1–3 additional carbocyclic or heterocyclic rings; wherein $K^2$ is a straight chain or branched chain, cyclic or acyclic, saturated or unsaturated or aromatic carbon- and/or heteroatom-containing moiety, which moiety is bound to $N^1$ via a carbon atom of the moiety and which contains 1 to about 40 carbon atoms, not more than about 20 halogen atoms and not more than 8 heteroatoms selected from the group consisting of oxygen, nitrogen, silicon, phosphorus and sulfur, this moiety being optionally connected to $K^1$ to form an additional carbocyclic or heterocyclic ring; wherein $K^3$ is hydrogen or a straight chain or branched chain, cyclic or acyclic, saturated or unsaturated or aromatic carbon- and/or heteroatom-containing moiety containing not more than 30 carbon atoms, not more than 24 halogen atoms and not more than 8 heteroatoms selected from the group consisting of oxygen, nitrogen, silicon, phosphorus and sulfur, said moiety being optionally connected to either $K^4$ or $K^1$ to form an additional ring; and wherein $K^4$ is hydrogen or a straight chain or branched chain, cyclic or acyclic, saturated or unsaturated or aromatic carbon- and/or heteroatom-containing moiety containing not more than 20 carbon atoms, not more than 24 halogen atoms and not more than 9 heteroatoms selected from the group consisting of oxygen, nitrogen, silicon, phosphorus and sulfur, the moiety being optionally connected to $K^3$ to form an additional ring.

$G_x$ is a moiety other than hydrogen, which is bound to the oxygen atom attached to position 14 via a carbon atom of $G_x$ and is selected from the group consisting of substituted or unsubstituted, straight or branched, acyclic or cyclic alkyls, alkenyls and alkynyls and substituted or unsubstituted aryls and aralkyls containing not more than about 30 carbon atoms, not more than 15 halogen atoms and not more than 8 heteroatoms selected from the group consisting of oxygen, nitrogen, silicon, phosphorus and sulfur. In a preferred embodiment, carbon 14 of $P_I$, the oxygen atom and the carbon atom of $G_x$ which is attached to 14-O form an ether linkage.

A preferred embodiment of $P_I$ comprises $P_V$ wherein $P_V$ is

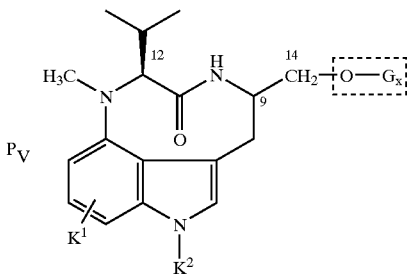

wherein $K^1$, $K^2$ and $G_x$ are as defined above.

The resultant compounds, in any case, generally display, variously, the protein kinase C-modulatory, protein kinase C isotype selective, non-toxic agonist, and/or antagonistic properties and utilities described in this invention.

It will be appreciated that the many different permissible changes to the hydroxymethyl and $N^1$ groups of the parent indolactam lead to somewhat diverse compounds with diverse biological properties, and different embodiments will be preferred for different utilities. If different protein kinase C isotypes and other proteins bearing phorboid-type binding sites have different biological functions, as has been extensively hypothesized and to some extent demonstrated in biological experiments, then the novel compounds of this invention with differing activity on different protein kinase C isotypes will obviously display a wide range of differing utilities, and certain such embodiments will variously be preferred for one or another utility.

An example of a particularly preferred embodiment of the present invention, for use in distinguishing protein kinase C isotypes and as anti-inflammatory agents consists of $P_I$ wherein $K^2$ is a generally hydrophobic substituent containing from about 4 to about 30 carbon atoms, from zero to about 15 halogen atoms and from zero or one to about four heteroatoms selected from the group consisting of oxygen, nitrogen, sulfur, phosphorus and silicon, and wherein $G_x$ is a small, charged or uncharged, polar or nonpolar group, consisting of substituents ranging from methyl to larger moieties containing as many as about ten carbon atoms, zero to about five halogen atoms and zero to about three heteroatoms selected from the group consisting of oxygen, nitrogen, sulfur, phosphorus and silicon and wherein $G_x$ is part of an ether group.

The compounds of this invention have been found to possess valuable pharmacological properties for human and veterinary medicine. For therapeutic use in humans or animals the compounds of this invention are dispensed in unit dosage form comprising 0.001 to 1000 mg per unit dosage in a pharmaceutically acceptable carrier. In particular, unit dosages in the range of 0.1 to 100 mg are preferred. The compounds of this invention may also be incorporated in topical formulations in concentrations of about 0.001 to 10 weight percent, with concentrations of 0.01 to 10 weight percent being preferred.

It will be appreciated that the actual preferred amounts of active compound in a specific case will vary according to the specific compound being utilized, the particular compositions formulated, the mode of application, and the particular sites and organism being treated. Compounds of this invention having higher potencies should be used in generally smaller amounts, and compounds with lower potencies should be used in generally larger amounts. Dosages for a given host, whether a small animal such as a cat or a human patient, can be determined using conventional considerations, e.g., the host's weight or body surface area. In general, the compounds of the present invention are administered in quantities of about 0.0001 to about 1000 mg/kg of body weight, and quantities of about 0.01 to about 100 mg/kg of body weight are preferred.

As specific examples, representative compounds of this invention variously block inflammation and show other utilities related to their protein kinase C-modulatory properties, such as an anti-psoriatic effect. These effects are demonstrated by inhibition in standard topical in vivo mouse ear inflammation tests wherein inflammation by established agonists such as PMA and the ionophore A23187 are blocked. These demonstrations of efficacy are achieved at doses per ear, per kg of body weight or per kg of bodily fluid equivalent, using numerous representative compounds of the present invention, of about 0.01–1000 nanogram/ear. Corresponding human doses are easily obtained by relating the activity of a standard anti-inflammatory compound such as dexamethasone on the mouse ear to standard human doses of dexamethasone, and using the resulting factor to translate the mouse ear anti-inflammatory activity of a compound of this invention into similar human doses. Obviously there may be slight differences for given compounds of this invention due to differential absorption or metabolism, but the mouse ear experiments can be performed in a matter of hours by workers of ordinary skill for compounds of this invention.

The compounds of this invention also show selective effects as antagonists for protein kinase C in some cases, as noninflammatory agonists for protein kinase C in other cases and biological settings and as selective ligands for protein kinase C and/or for phorboid receptors.

Thus, these compounds can be used as agents for the abrogation of protein kinase C-related pathophysiological conditions and disease states in applications such as anti-inflammatory, anti-psoriatic, anti-cancer, anti-ulcer, anti-hypertensive, anti-asthma, anti-arthritic, anti-autoimmune, anti-nociceptive, anti-secretory, anti-parasitic, anti-amoebic, anti-viral including anti-HIV replication, in prophylaxis against infection by any HIV form and any other application in which pathological involvement of protein kinase C is found.

Furthermore, the non-inflammatory agonists among the compounds of this invention may be used to achieve desired physiological results such as interferon release, interleukin induction, tumor necrosis factor production, immune system stimulation and/or reconstitution, insulin secretion, insulinomimetic activity, acceleration of wound healing, improvement in central nervous system functions, such as memory and learning and abrogation of the symptoms or progress of Alzheimer's disease, and any other application for which desirable actions of protein kinase C are found.

As phorboid receptor subtype- and/or protein kinase C subtype-selective ligands, the compounds of this invention also have very valuable application as experimental agents for research into the role of protein kinase C and/or phorboid receptors in important biological processes and in human and veterinary diseases. Thus, their value extends to their use as pharmacological tools for in vitro and in vivo research, in a manner similar to the important roles that selective agonists and antagonists have played in the studies of the mechanism of action of adrenergic, dopaminergic, opiate, benzodiazepine, cholinergic and serotoninergic receptor systems, among others.

In addition, the compounds can be used in in vitro diagnostics (e.g., in an assay for protein kinase C). They are also useful as intermediates in the production of other drugs, e.g., as described in the present invention.

The compounds of this invention are generally administered to animals, including but not limited to fish, avians and mammals including humans.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients and carriers, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcoholics, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., enzyme inhibitors, to reduce metabolic degradation. Such carriers do not include the following solvents when used alone: dimethylsulfoxide, acetone or methanol or ethanol of greater than 80% concentration in water.

When compounds of the present invention are provided as part of a pharmaceutical composition, many of the specifically stated exceptions enumerated in the previous detailed description of the compounds, themselves, are no longer needed. This occurs because the enumerated exceptions were known to be in the prior art as synthetic intermediates or as compounds believed to have no pharmacological activities. In the present invention, these compounds, as part of pharmaceutical compositions, have antiviral activities or anti-inflammatory activities, etc. That is, the pharmaceutical composition formulation confers an inventive significance to these compounds.

For parenteral application, particularly suitable are injectable, sterile solutions, preferably oily or aqueous solutions, as well as suspensions, emulsions or implants, including suppositories. Ampoules are convenient unit dosages.

For enteral application, particularly suitable are tablets, dragees, liquids, drops, suppositories or capsules. A syrup, elixir, or the like can be used wherein a sweetened vehicle is employed.

A preferred method of administration comprises oral dosing, with tablets, dragees, liquids, drops, or capsules. For the oral route of administration, either compounds of this invention lacking functional groups destroyed by acid or tablets or capsules which protect the active compound from upper gastrointestinal acidity are preferred.

Sustained or directed release compositions can be formulated, e.g., in liposomes or in compositions wherein the active compound is protected with differentially degradable coatings, e.g., by microencapsulation, multiple coatings, absorption onto charcoal, entrapment in human serum albumin microspheres, etc. It is also possible to freeze-dry the new compounds and use the lyophilizates obtained, for example, for the preparation of products for injection.

Another preferred route of administration comprises topical application, for which are employed nonsprayable forms, viscous to semi-solid or solid forms comprising a carrier compatible with topical application and having a dynamic viscosity compatible with topical application, preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The compounds of this invention, admixed with appropriate carriers, may also be delivered to subjects by means of an externally connected or internally implanted pumping device to give a controlled and/or sustained release of the therapeutic mixture or by means of a patch of natural or synthetic fabric and/or polymer impregnated with the compounds in a suitable carrier and affixed to the skin to achieve transdermal release and absorption of the active compounds.

The compounds of this invention may also be modified by covalent attachment of metabolically modifiable groups, to form "prodrugs" which are released by cleavage in vivo of the metabolically removable groups. For example, amine, hydroxy and/or thiol groups present in many compounds of this invention may be converted to prodrugs by covalent attachment of acyl or aminoacyl organic functional groups. Likewise, compounds of this invention containing carboxylic, sulfonic, phosphoric, phosphonic or related free acids, including those in which one or more oxygen atoms are replaced by sulfur, may be converted to prodrugs by formation of their esters or amides by covalent attachment of alcohols, amines, amino acids and the like. Compounds of this invention may also incorporate N-alkyldihydropyridine functional groups, which become localized to the central nervous system after administration to the subject and subsequent metabolic modification of the N-alkyldihydropyridine group in the central nervous system.

It will be recognized by persons with ordinary skill in medicinal chemistry that conversion of alcohol-, amine-, thiol- or acid-containing compounds of this invention to prodrugs is preferably done by derivatization of such groups located in regions of the molecule having minimal steric hindrance, to permit access of metabolizing enzymes, other bioreactants or water. Such alcohol-, amine-, thiol- or acid-containing groups may be located in any of the parent, side-chain or capping-group organic functional groups described above. A prodrug-type group such as the N-alkyldihydropyridine group, however, is preferably added to the parent structure, $P_f$, unless it is found for a given compound that the N-alkyldihydropyridine group and/or its metabolic pyridinium oxidation product has desirable bioactivity when located in the side chain ($G_x$) of a compound of this invention.

It will be appreciated that starting materials for obtaining compounds of this invention from natural sources or from total or partial synthesis may be altered in very diverse ways, consistent with this invention, to obtain compounds with novel and diverse primary biological/medicinal activities resulting from, and controlled by, the specific new $K^2$ and $G_x$ groups set forth above; such properties include, for example, loss of skin inflammatory activity and appearance or retention of anti-inflammatory, anti-psoriatic and other activities. It is also possible to introduce an extremely wide variety of changes into the substituent on $N^1$ of the indolactam nucleus, into the substituent at 14-O with modest variety, and into other regions of the indolactam structure to obtain new entities with improved secondary properties, such as, variously, hydrophobicity, water solubility, potency, oral availability, metabolic and chemical stability, reduced therapeutic side effects and so on, using strategies and techniques widely recognized in the art of medicinal chemistry and pharmacology.

Starting materials for the synthesis of the compounds of this invention from the indolactam ($P_I$) class of phorboids may be obtained from any of a variety of natural sources as described in the literature {T. Sugimura, *Gann* 73: 499–507 (1982), H. Fujiki and T. Sugimura, *Advances in Cancer Research* 49: 223–264 (1987), K. Irie and K. Koshimizu, *Mem. Coll. Agric., Kyoto Univ.* 132: 1–59 (1988) and references cited therein}. Furthermore, these indolactam phorboids are available by total synthesis from common organic chemical starting materials. These syntheses provide a considerable variety of approaches and associated flexibility in arriving at highly diverse functionalities on the parent nucleus and on the final $K^2$ or $G_x$ substituents, and include, but are not limited to, the procedures described by Y. Endo et al., *Tetrahedron* 42: 5905–5924 (1986), S. de Laszlo et al., *J. Chem. Soc., Chem. Comm.* 344–346 (1986), S. Nakatsuka et al., *Tetrahedron Letters* 27: 5735–5738 (1986) and *Tetrahedron Letters* 28: 3671–3674 (1987), H. Muratake and M. Natsume, *Tetrahedron Letters* 28: 2265–2268 (1987), M. Mascal and C. Moody, *J. Chem. Soc., Chem. Comm.* 589–590 (1988), A. Kozikowski et al., *J. Am. Chem. Soc.* 111: 6228–6234 (1989), T. Kogan et al., *Tetrahedron* 46: 6623–6632 (1990), and J. Quick et al., *Tetrahedron Letters* 35: 8549–8552 (1994) and references therein.

It is obvious to one skilled in the art that many of these published syntheses may be readily modified to provide parent-modified hydroxymethyl or non-hydroxymethyl containing compounds which may be useful examples of the invention and/or may be the starting materials for further modification. For example, the methods described by Quick et al (op cit.) are particularly useful for the preparation of indolactams which are stereochemical isomers of (−)-indolactam V {(9S,12S)-indolactam V}, i.e., (+)-indolactams {(9R,12R)-indolactams}, (−)-epi-indolactams {(9R,12S)-indolactams} and (+)-epi-indolactams {(9S,12R)-indolactams}. As a further example, modifications of the Endo-procedure (Y. Endo, et al., op cit.) have been used to prepare (±)-indolactam G, (±)-indolactam A, (±)-indolactam F, (±)-indolactam L and (±)-indolactam $t_L$ where the isopropyl group of ILV has been replaced by hydrogen, methyl, benzyl, isobutyl and t-butyl respectively {Y. Endo, et al., *Tetrahedron* 43: 3695–3704 (1987)}.

Given indolactams containing hydroxymethyl groups, the means for modifying the hydroxymethyl group and the $N^1$-position to produce the compounds of this invention will be obvious to workers with ordinary skill in synthetic organic chemistry.

Many variations for the formation of ethers at position 14 can be found in standard organic synthesis texts such as J. March, *Advanced Organic Chemistry*, Third Edition, Wiley-Interscience, New York, 1985 or in monographs such as S. R. Sandier and W. Karo, *Organic Functional Group Preparation—I*, Second Edition, Academic Press, San Diego, 1983 (see pages 129–146). Such methods include, but are not limited to, the Williamson ether synthesis, the condensation of alcohols with olefins, acetylenes and oxides and dehydration. A particular method of dehydration is the alkylation of phenolic hydroxyls with alcohols in the presence of diethyl azodicarboxylate and triphenylphosphine known as the Mitsunobu reaction {see O. Mitsunobu, *Synthesis* 1–28 (1981)}.

In some cases, the hydroxymethyl group may be modified once other regions of the molecule have been suitably protected using simple, obvious and widely-precedented methodologies practiced extensively in synthetic organic chemistry. In some specific cases the indole nitrogen must be blocked before some types of chemical modifications may be accomplished on the hydroxymethyl group or on other portions of the indolactam parent. Many protecting groups for the indole nitrogen have been used in the organic chemical literature, and their use here is obvious. Among these are t-butoxycarbonyl, acetyl, benzyl, trimethylsilylethoxy-methylene, benzyloxycarbonyl and benzenesulfonyl, which are variously stable to or removed under acidic, basic or reducing conditions or with fluoride ion reagents.

An anion of the hydroxy group of protected and unprotected parent indolactams may be formed in several ways and treated with a wide range of electrophiles. Persons of ordinary skill in the art of organic synthesis will recognize that such electrophiles may include, without limitation, reagents such as unsubstituted or substituted alkyl, alkenyl, alkynyl, cycloalkyl and benzyl halides, p-toluenesulfonates or methansulfonates or carboxylic acid derivatives. For example, (−)-14-O-methylindolactam V may be prepared by treatment of (−)-indolactam V with sodium metal in toluene at 100° C. followed by the addition of methyl p-toluenesulfonate (K. Irie and K. Koshimizu, op cit.). Alkylation of (−)-14-O-methylindolactam V with benzylbromide in the presence of sodium hydride in a N,N-dimethylformamide solution affords $N^1$-benzyl-14-O-methyl-(9S,12S)-indolactam V. $N^1$ and 14-O symmetrically substituted indolactams may be prepared in one step by the use of excess electrophile in the presence of sodium hydride in N,N-dimethylformamide. Thus, $N^1$, 14-O-digeranyl-(9S,12S)-indolactam V may be prepared by treatment of (−)-indolactam V with geranyl bromide as described in Example 8.

The use of a protecting group on $N^1$ also allows the alkoxide to be selectively formed at 14-O which may then be selectively treated with an electrophile. As an example N[1]-t-butyloxycarbonylindolactam V (see Example4) when treated with 2-hexynyl p-toluenesulfonate in the presence of sodium hydride in N,N-dimethylformamide affords N[1]-t-butyloxycarbonyl-14-O-(2'-hexynyl)-(9S,12S)-indolactam V which is a useful compound of this invention. N[1]-t-butyloxycarbonyl-14-O-(2'-hexynyl)-(9S,12S)-indolactam V may be treated further by removing the BOC group under acidic conditions and alkylating the resulting product with ethyl p-toluenesulfonate in the presence of sodium hydride which affords N[1]-ethyl-14-O-(2'-hexynyl)-(9S,12S)-indolactam V. The final N[1]-substituent may also serve as an appropriate "blocking group" allowing selective modification of the hydroxymethyl group or other portions of the indolactam nucleus. An example is the preparation of N[1]-(2,4-difluorobenzyl)-14-O-methyl-(9S,12S)-indolactam V from N[1]-(2,4-difluorobenzyl)-(9S,12S)-indolactam V in Example 11.

Conversion of the hydroxy group to a halogen or pseudohalogen permits the displacement of the resultant electrophile from the protected or in some cases, unprotected, parent nucleus by a very wide range of nucleophiles as in a Williamson-type ether synthesis. Persons with ordinary skill in the art of organic synthesis will recognize that such nucleophiles may include, without limitation, reagents having carbon, hydrogen, oxygen, nitrogen, sulfur, phosphorus, silicon, arsenic, boron, and/or selenium atoms in their structures. Particular examples would be reaction with ammonia, methylamine, the sodium salt of dimethylphosphine, trimethylphosphite, triphenylphosphine, potassium sulfite, trimethylsilylmethyl-metal salts, lithium trimethylsilylacetylide, sodium cyanide, N-methyl-2-hydroxyethyl amine, 1[H]-tetrazole, or with the sodium salt of 2-mercaptoethanol, 3-mercaptoethanol, or of hydroxymethylphenol. Many variations may be executed as described in standard textbooks of synthetic organic chemistry, such as J. March, op cit. As an illustration, treatment of 14-O-methanesulfonyl-N[1]-(2'-trans-heptenyl) indolactam V with the sodium salt of 4-t-butyldimethylsilyloxy-2-phenylphenol followed by treatment of the product with tetrabutylammonium fluoride in tetrahydrofuran affords 14-O-(4'-hydroxy-2'-phenyl)phenyl-N[1]-(2'-trans-heptenyl)indolactam V. In a similar manner 14-O-(5'-hydroxy-1'-naphthyl)-N[1]-benzylindolactam V, 14-O-(3'-hydroxy-5'-benzyloxy)phenyl-N[1]-octylindolactam V, 14-O-(4'-hydroxy-2'-phenyl)phenyl-6,7-tetramethyleneindolactam V, 14-O-(5'-hydroxy-1'-naphthyl)-6,7-tetramethyleneindolactam V, 14-O-(3'-hydroxy-5'-benzyloxy)phenyl-6,7-tetramethyleneindolactam V are prepared. See Y. Endo et al., *Tetrahedron* 42: 5905–5924 (1986) for a synthesis of 6,7-tetramethyleneindolactam V.

By use of protecting groups or modifications of the indolactam parent by methods well-known in the art of synthetic chemistry, the hydroxy group of the hydroxymethyl may be replaced by a metal and then reacted with an electrophile, effectively replacing the hydroxy with a group derived from the electrophile. The techniques for this replacement are obvious to workers with ordinary skill in organic synthesis, in that replacement of the hydroxymethyl hydroxy group by halogen in a suitably protected or modified indolactam permits strong and/or hard nucleophiles to be generated by the use of metals or strong bases, and persons with ordinary skill in the art of organic chemistry will recognize that such nucleophiles can be contacted with a very diverse range of electrophilic reagents having carbon, hydrogen, oxygen, nitrogen, sulfur, phosphorus, silicon, arsenic, boron and/or selenium atoms in their structures to obtain hydroxymethyl-modified indolactams of widely varying structures.

Alternatively, the hydroxy group on the hydroxymethyl of appropriately protected or modified indolactams may be oxidized to an aldehyde and then reacted via condensation or addition chemistries to provide a very wide variety of modified indolactams. Examples, without limitation, would be reactions with Wittig reagents, hydroxylamines or Grignard reagents. Many variations may be executed as described in standard textbooks of synthetic organic chemistry, such as J. March, op cit. These aldehydes may also be obtained by reduction of appropriate carboxylic acid derivatives by application of well-known techniques.

The hydroxymethyl group of suitable indolactam phorboids may be oxidized to the carboxylic acid level by methods well-known in the art or these carboxylic acids may be prepared by modifications of the total syntheses described in the literature cited above. These acids permit the preparation of further modified indolactams.

The total syntheses described in the literature cited above are also amenable to extensive adaptations so as to provide a wide variety of modifications in the parent structures of the indolactam group. By established techniques in the art of organic synthesis modified parent structures may be obtained which embody alterations at the hydroxymethyl group and which have useful biological activity. This extremely wide variety of modified indolactam structures may result from the use of modified starting materials, from modifications of one or more synthetic steps or from a combination of both. As an illustration, 9-deshydroxymethyl-9-methoxycarbonyl-6,7-tetramethyleneindolactam V may be prepared from 4-nitro-6,7-tetramethylene-gramine (Y. Endo et al., op cit.) by the application of several routes obvious to workers with ordinary skill in organic synthesis. For example, methyl α-nitro-4-amino-6,7-tetramethyleneindole-3 acetate is prepared from 4-nitro-6,7-tetramethylenegramine in the manner described by T. Masuda et al., *Agric. Biol. Chem.* 53: 2257–2260 (1989). Alkylation of the amino group of this compound with benzyl D-α-trifluoromethylsulfonyloxyisovalerate in the manner described by T. Kogan et al., op cit., affords an optically active intermediate which, after removal of the benzyl ester and reduction of the nitro group, is lactamized in the manner of T. Masuda et al., op cit., and methylated by treatment with formaldehyde/sodium cyanoborohydride to afford 9-deshydroxymethyl-9-methoxycarbonyl-6,7-tetramethylene-(9S,12S)-indolactam V. Reduction with lithium borohydride affords 6,7-tetramethylene-(9S,12S)-indolactam V from which may be prepared compounds of this invention by methods described above and below.

To further illustrate the synthesis of the compounds of this invention, the modified indolactam, 1,2,4,5,6,8-hexahydro-5-butoxymethyl-2-(1-methylethyl)-3H-(N-ethyl)pyrrolo(4,3,2-gh)-1,4-benzodiazonin-3-one, may be prepared from N-BOC-4-nitrotryptophanol {Y. Endo et al., *Tetrahedron* 42: 5905–5924 (1986)} by the application of several routes obvious to workers with ordinary skill in synthetic chemistry. For example, preparation of N-BOC-O-butyl-N[1]-ethyl-4-nitrotryptophanol may be accomplished by alkylation of the indole nitrogen with ethyl p-toluenesulfonate in the presence of sodium hydride followed by O alkylation with butylbromide in the presence of sodium hydride or sodium metal or by several other routes. From the butoxy derivative the synthesis could proceed in the manner described by Y. Endo et al., loc cit., for the hydroxy derivative. Specifically, the resulting substituted indolylvaline methyl ester is hydrolyzed and the resulting acid is converted to the N-succinimidyl ester. Upon cleavage of the BOC group under acidic conditions cyclization to the lactam occurs directly to provide all four stereoisomers, i.e., 2R,5R-, 2R,5S-, 2S,5S-, and 2S,5R-1,2,4,5,6,8-hexahydro-5-butoxymethyl-2-(1-methylethyl)-3H-(N-ethyl)pyrrolo (4,3,2-gh)-1,4-benzodiazonin-3-one. These stereoisomers may be obtained separately either by beginning the synthesis with optically active N-BOC-4-nitrotrytophanol or by separation from the mixture by chromatography on an enantioselective column packing {D. Armstrong, *Analytical Chem.* 59: 84–91A (1987)}. Similarly, the further modified indolactam, 1-(1-oxobutyl)-1,2,4,5,6,8-hexahydro-5-butoxymethyl-3H-(N-ethyl)pyrrolo(4,3,2-gh)-1,4-benzodiazonin-3-one, may be prepared. Specifically, hydrogenation of N-BOC-O-butyl-$N^1$-ethyl-4-nitrotrytophanol over palladium on carbon will provide N(2')-BOC-O-butyl-$N^1$-ethyl-4-aminotrytophanol. Alkylation of this compound with methyl bromoacetate affords N-{3-($N^2$-BOC-2'-amino-3'-butoxypropyl)-$N^1$-ethyl-4-indolyl}glycine methyl ester {Y. Endo, et al., *Chem. Pharm. Bull.* 30: 3457–3460 (1982)}. Acylation of this material with butanoyl chloride in the presence of potassium carbonate or pyridine will provide N-butanoyl-N-{3-($N^2$-BOC-2'-amino-3'-butoxypropyl)-$N^1$-ethyl-4-indolyl}glycine methyl ester. This latter material may be converted to 1-(1-oxobutyl)-1,2,4,5,6,8-hexahydro-5-butoxymethyl-3H-(N-ethyl)pyrrolo(4,3,2-gh)-1,4-benzodiazonin-3-one by application of the methods of Y. Endo, et al., loc cit. (1986). The enantiomers, 5R- and 5S-, may be obtained separately by beginning with optically active materials as described above or by separation at the final stage by chromatography also as described above.

As a further illustration, $N^1$-phenylindolactam V may be prepared by introduction of the $N^1$-substituent very early in the synthesis and used to prepare compounds of the invention. One preparation of this parent begins with the preparation of $N^1$-phenylindole from N,N-diphenylhydrazine and ethyl pyruvate by a Fisher indole synthesis (B. Robinson, "The Fisher Indole Synthesis," John Wiley & Sons, NY. 1982. page 400.). $N^1$-phenyl-4-nitrotryptophanol is prepared from $N^1$-phenylindole by application of standard tryptophan synthetic schemes including the nitration of $N^1$-phenyl-3-oxalylindole. The $N^1$-phenylindolactam V is then prepared by a route similar to that presented in the paragraph just above.

It is obvious to one skilled in the art that many indolactam parents, modified at positions other than $N^1$ or 14-O, may be obtained by carrying a modification through the de novo synthesis as described in the literature cited above. As an illustration, 7-alkylindolactam Vs containing a wide variety of alkyl groups may be prepared by application of the method of A. Kozikowski et al., op cit., to a variety of alkyl substituted isoxazolines. As a further illustration, the modified indolactam, 1-(ethyl)-1,2,4,5,6,8-hexahydro-5-hydroxymethyl-3H-pyrrolo{4,3,2-gh}-1,4-benzodiazonin-3-one ($N^{13}$-ethylindolactam G), may be prepared. Alkylation of 4-aminoindole with methyl bromoacetate followed by acylation with acetyl chloride in the presence of pyridine affords N-acetyl-N-(4-indolyl)glycine methyl ester. This is converted to $N^{13}$-ethylindolactam G by the method described by A. Kozikowski et al., op cit. The enantiomers are obtained separately by silica gel chromatography of the 14-O-{N-(S)-(1'-naphthyl)ethyl}carbamates followed by reduction with trichlorosilane-triethylamine. Further modifications of this material to produce hydroxymethyl modified embodiments of this invention are carried out by the preparation of 1-N-(t-butyloxycarbonyl)-$N^{13}$-ethylindolactam G, according to the method of Y. Endo et al., *Tetrahedron* 43: 2241–2247 (1987). Then, 14-O-methanesulfonyl-1-N-(t-butyloxycarbonyl)-$N^{13}$-ethylindolactam G may be prepared by treatment of the above indolactan with methanesulfonyl chloride. Treatment of this material with a variety of nucleophiles as described above followed by removal of the t-butyloxycarbonyl group by treatment with acid, for example trifluoroacetic acid in methylene chloride, affords a very wide variety of hydroxymethyl-modified derivatives. 14-O-Phenyl-$N^{13}$-ethylindolactam G is a specific illustration of the type of useful compounds which may be prepared by application of these approaches. These may be readily converted to compounds of the invention by replacing the hydrogen on $N^1$ with another substituent as described above and below.

Further synthetic elaborations may be effected at the end or near the end of the preparation of the modified indolactam-parent or of the hydroxymethyl-modified indolactam. An illustration of the modification of the parent group after the introduction of appropriate hydroxymethyl modifications is the preparation of $N^1$-cinnamyl-14-O-(3',7'-dimethyloctyl)indolactam V from 14-O-geranylindolactam V via hydrogenation over palladium followed by alkylation with cinnamyl bromide. A further example is the preparation of $N^1$-hexanoyl-14-O-methylindolactam A by treatment of the sodium salt of 14-O-methylindolactain A with hexanoic anhydride.

The application of established techniques in the art of synthetic chemistry to naturally derived or to synthetically derived parents of the indolactam group also permits the obtainment of specifically modified parents of that class. These modified parents may then be further modified at the hydroxymethyl group by the methods discussed above. To illustrate this, 14-O-t-butlydimethylsilylindolactam V {Y. Endo et al., *Tetrahedron* 43: 2241–2247 (1987)} may be treated with sodium hydride in dimethylformamide followed by phosgene. The reactive chloroformamide so formed is quenched with perfluoroheptylmethanol to afford, after removal of the silyl ether, 1-N-(pentadecafluoro-{1H,1H}-octyloxy)carbonylindolactam V. By application of methods discussed above a variety of hydroxymethyl modified derivatives may be prepared as specifically illustrated by 14-O-prenyl-$N^1$-(pentadecafluoro-{ 1H,1H}-octyloxy) carbonylindolactam V and by 14-O-(pentadecafluoro-{1H,1H}-octyl)-$N^1$-(pentadecafluoro-{ 1H,1H}-octyloxy) carbonylindolactam V. As a further illustration, 14-O-acetylindolactam V {K. Irie and K. Koshimizu, *Mem. Coll. Agric., Kyoto Univ.* 132: 1–59 (1988)} may be alkylated with ethyl acrylate in the presence of sodium hydride to afford 14-O-acetoxy-$N^1$-(2'-ethoxycarbonyl)indolactam V. Treatment of this material with aluminum chloride in nitrobenzene followed by reduction of the purified product with lithium aluminum hydride-aluminum chloride in tetrahydrofuran provides 1,7-trimethyleneindolactam V. By application of methods discussed above a variety of hydroxymethyl modified derivatives may be prepared as specifically illustrated by 14-O-allyl-1,7-t methyleneindolactam V and by 14-O-phenyl-1,7-trimethyleneindolactam V.

Such specifically modified parents of the indolactam class may also be further modified at positions other than the hydroxymethyl group either before or after the modifications of hydroxymethyl group. The means for accomplishing these modifications are obvious to workers with ordinary skill in organic synthesis.

This invention is illustrated further by the following examples.

EXAMPLE 1

N$^1$,14-O-Diethyl-(9S,12S)-indolactam V

To a suspension of 29 mg (0.43 mmol) of 60% sodium hydride in 0.66 mL of N,N-dimethylformamide at 0° C. was added 120 mg (0.29 mmol) of (−)-14-O-tert-butyldimethylsilylindolactam V {Endo, Y., et al. *Tetrahedron* 43: 2241–2247 (1987)}. After 10 min, 86 mg (0.43 mmol) of ethyl p-toluenesulfonate in 0.66 mL N,N-dimethylformamide was added. The reaction mixture was stirred for 30 min at room temperature. The N,N-dimethylformamide was removed in vacuo at room temperature and the residue was partitioned between methylene chloride and water. The organic layer was separated, dried over magnesium sulfate and concentrated in vacuo to yield an oily residue. The residue was dissolved in 5 mL dry tetrahydrofuran and treated with 0.5 mL (0.5 mmol) of 1 M tetrabutylammonium fluoride in tetrahydrofuran. After stirring for 30 min, the mixture was concentrated in vacuo. The residue was partitioned between water and methylene chloride. The organic layer was dried over sodium sulfate and concentrated in vacuo to a brown residue. This residue was subjected to preparative liquid chromatography {0.5×1' column; silica; hexane/ethyl acetate (70:30)} to afford 39.6 mg (0.11 mmol; 38% yield) of N$^1$,14-O-diethyl-(9S,12S)-indolactam V which was characterized by NMR and mass spectra.

EXAMPLE 2

N$^1$,14-O-Dioctyl-(9S,12S)-indolactam V

To a suspension of 28 mg (0.43 mmol) of 60% sodium hydride in 0.66 mL of N,N-dimethylformamide at 0° C. was added 120 mg (0.29 mmol) (−)-14-O-tert-butyldimethylsilylindolactam V. After 10 min, 103 mg (0.43 mmol) of iodooctane in N,N-dimethylformamide was added. The reaction mixture was stirred overnight at room temperature, then heated at 80° C. for 3 hr. The N,N-dimethylformamide was removed in vacuo and the residue was partitioned between methylene chloride and water. The organic layer was separated, dried over magnesium sulfate and concentrated in vacuo. The residue was dissolved in 5 mL dry tetrahydrofuran and treated with 1 mL (1 mmol) of 1M tetrabutylammonium fluoride in tetrahydrofuran. The mixture was concentrated in vacuo, the residue was diluted with water and extracted with methylene chloride. The organic layer was dried over sodium sulfate and concentrated in vacuo. The residue was subjected to preparative liquid chromatography {0.5×1' column; silica; hexane/ethyl acetate (80:20)} to afford 23 mg (44 μmol; 15% yield) of N$^1$,14-O-dioctyl-(9S,12S)-indolactam V.

EXAMPLE 3

N$^1$,14-O-Digeranyl-(9S,12S)-indolactam V

To a suspension of 28 mg (0.43 mmol) of 60% sodium hydride in 0.66 mL of N,N-dimethylformamide at 0° C. was added 120 mg (0.29 mmol) (−)-14-O-tert-butyldimethylsilylindolactam V. After 10 min, 93 mg (0.43 mmol) of geranyl bromide in 0.66 mL of N,N-dimethylformamide was added. The reaction mixture was stirred overnight at room temperature, then the N,N-dimethylformamide was removed in vacuo and the residue was partitioned between methylene chloride and water. The organic layer was separated, dried over magnesium sulfate and concentrated in vacuo. The residue was dissolved in 5 mL dry tetrahydrofuran and treated with 1 mL (1 mmol) of 1M tetrabutylammonium fluoride in tetrahydrofuran. After stirring for a brief time the mixture was concentrated in vacuo. The residue was diluted with water and extracted with methylene chloride. The organic layer was dried over sodium sulfate and concentrated in vacuo. The residue was subjected to preparative liquid chromatography {0.5×2' column; silica; hexane/tetrahydrofuran (77:23)} to afford 9 mg (16 μmol; 5% yield) N$^1$,14-O-digeranyl-(9S,12S)-indolactam V which was characterized by NMR and mass spectra.

EXAMPLE 4

N$^1$,14-O-Dicinnamyl-(9S,12S)-indolactam V

To a suspension of 83 mg (2.1 mmol) of 60% sodium hydride in 1.5 mL of N,N-dimethylformamide at 0° C. was added 100 mg (0.24 mmol) of (−)-14-O-tert-butyldimethylsilylindolactam V. After 10 min, 200 mg (1 mmol) of cinnamyl bromide in was added. The reaction mixture was stirred for 30 min at 0° C. then the N,N-dimethylformamide was removed in vacuo and the residue was partitioned between methylene chloride and water. The organic layer was separated, dried over sodium sulfate and concentrated in vacuo to yield crude silylated intermediate {R$_f$=10.79; silica; hexane/ethyl acetate (67:33)}. The residue was dissolved in 5 mL dry tetrahydrofuran and treated with 1 mL (1 mmol) of 1M tetrabutylammonium fluoride in tetrahydrofuran. After stirring for 30 min, the mixture was concentrated in vacuo. The residue was partitioned between water and methylene chloride. The organic layer was dried over sodium sulfate and concentrated in vacuo. This residue was subjected to preparative liquid chromatography {0.5×1' column; silica; hexane/ethyl acetate (70:30)} to afford 24.6 mg (46 μmol; 19% yield) of N$^1$,14-O-dicinnamyl-(9S,12S)-indolactam V the structure of which was established by NMR and mass spectra.

EXAMPLE 5

N$^1$,14-O-Di(4'-tert-butylbenzyl)-(9S,12S)-indolactam V

To a suspension of 83 mg (2.1 mmol) of 60% sodium hydride in 1.5 mL of N,N-dimethylformamide at 0° C. was added 100 mg (0.24 mmol) of (−)-14-O-tert-butyldimethylsilylindolactam V. After 10 min, 200 mg (0.88 mmol) of 4-t-butylbenzylbromide in 1.5 mL N,N-dimethylformamide was added. The reaction mixture was stirred for 30 min at 0° C. The N,N-dimethylformamide was removed in vacuo at room temperature and the residue was partitioned between methylene chloride and water. The organic layer was separated, dried over sodium sulfate and concentrated in vacuo to yield a crude silylated dialkylindolactam V {R$_f$=0.82; silica; hexane/ethyl acetate (67:33)}. The residue was dissolved in 5 mL dry tetrahydrofuran and treated with 1 mL (1 mmol) of 1M tetrabutylammonium fluoride in tetrahydrofuran. After stirring for 30 min, the mixture was concentrated in vacuo. The residue was partitioned between water and methylene chloride. The organic layer was dried over sodium sulfate and concentrated in vacuo. This residue was subjected to preparative liquid chromatography {0.5×1' column; silica; hexane/ethyl acetate (70:30)} to afford 89 mg (0.15 mmol; 29% yield) of N$^1$,14-O-di(tert-butylbenzyl)-(9S,12S)-indolactam V the structure of which was confirmed by NMR and mass spectra.

EXAMPLE 6

Ethylation of (−)-Indolactam V. Sodium/Toluene/Reflux

A mixture of 100 mg (0.33 mmol) of (−)-indolactam V, 400 mg (17 mmol) of sodium metal and 172 mg (0.85 mmol)

of ethyl tosylate in 7 mL of toluene was heated at reflux for 60 min. After the mixture had cooled to room temperature it was filtered and the filtrate diluted with ethyl acetate and washed with water and brine, then dried over sodium sulfate and concentrated in vacuo. The residue was subjected to preparative liquid chromatography {0.5×2' column; silica; hexane/ethyl acetate (70:30)} to afford 11 mg (31 µmol; 9.3% yield) of $N^1$,14-O-diethyl-(9S,12S)-indolactam V, 6 mg (18 µmol; 5.5% yield) of $N^1$-ethyl-(9S,12S)-indolactam V and 4 mg (12 µmol; 3.5% yield) of 14-O-acetylindolactam V. In addition 21 mg of mixture was obtained which was separated by reverse-phase liquid chromatography {C18; 10µ; acetonitrile/water (70:30)} to afford 8.4 mg (25 µmol; 7.7% yield) of 14-O-ethylindolactam V and 9.5 mg (25 µmol; 7.7% yield) of 14-O-acetyl-$N^1$-ethylindolactam V. The structures were assigned by NMR spectroscopy.

EXAMPLE 7

Ethylation of (−)-Indolactam V. Sodium Hydride/ Tetrahydrofuran/Reflux

A mixture of 100 mg (0.33 mmol) of (−)-indolactam V and 80 mg (2 mmol) of 60% sodium hydride in 8 mL of tetrahydrofuran was stirred at ambient for 10 min. Then 340 mg (1.7 mmol) of ethyl tosylate was added. The mixture was then heated at reflux for 4 h. After the mixture had cooled to room temperature overnight, it was concentrated in vacuo. The residue was partitioned between water and ethyl acetate. The organic layer was washed with brine, then dried over sodium sulfate and concentrated in vacuo. The residue was subjected to preparative liquid chromatography {0.5×2' column; silica; hexane/ethyl acetate (85:15)} to afford 3 mg (7.8 µmol; 2.3% yield) of $N^1$,$N^{10}$,14-O-triethylindolactam V, 38 mg (99 µmol; 30% yield) of $N^1$,11-O,14-O-triethylindolactam V and 32.6 mg (91 µmol; 28% yield) of $N^1$,14-O-diethyl-(9S,12S)-indolactam V. The structures were assigned by NMR spectroscopy.

EXAMPLE 8

$N^1$,14-O-Digeranyl-(9S,12S)-indolactam V (Method 2)

A solution of 25 mg (83 µmol) of (−)-indolactam V in 300 µL of dry N,N-dimethylformamide was added to 25 mg (0.6 mmol) of 60% sodium hydride in a 5 mL round-bottom flask maintained at 0° C. under nitrogen. After 10 minutes 40 mg (184 µmol) of geranyl bromide in 100 µL of N,N-dimethylformamide was added. After another 30 minutes the mixture was allowed to warm to room temperature and five hours later was diluted with methylene chloride and water. The organic layer was separated, filtered through layers of sodium chloride and sodium sulfate and concentrated in vacuo. The residue was combined with those from smaller scale reactions and subjected to preparative liquid chromatography {0.5×3' column; silica; hexane/tetrahydrofuran (75:25)} to afford 34 mg of $N^1$,14-O-digeranyl-(9S,12S)-indolactam V.

EXAMPLE 9

In a manner similar to those set forth above, the following compounds are prepared:

(i) $N^1$,14-O-di(t-butylethyl)-(9S,12S)-indolactam V;
(ii) $N^1$,14-O-diprenyl-(9S,12S)-indolactam V;
(iii) $N^1$,14-O-bis(2'-trans-heptenyl)-(9S,12S)-indolactam V;
(iv) $N^1$,14-O-dipropargyl-(9S,12S)-indolactam V;
(v) $N^1$,14-O-bis(2'-hexynyl)-(9S,12S)-indolactam V;
(vi) $N^1$,14-O-dibenzyl-(9S,12S)-indolactam V;
(vii) $N^1$,14-O-bis(2',4'-difluorobenzyl)-(9S,12S)-indolactam V;
(viii) $N^1$,14-O-bis(2'-trans-heptenyl)-(9R,12R)-indolactam V;
(ix) $N^1$,14-O-digeranyl-(9R,12S)-indolactam V;
(x) $N^1$,14-O-bis(3'-nitrobenzyl)-(9S,12R)-indolactam V;
(xi) $N^1$,14-O-bis(2'-trans-heptenyl)-(9R)-indolactam G;
(xii) rac-$N^1$,14-O-digeranyl-13-desmethyl-$N^{13}$-ethylindolactam G;
(xiii) $N^1$,14-O-digeranyl-(9S,12S)-indolactam L;
(xiv) $N^1$,14-O-bis(2'-pyridinemethyl)-(9S,12S)-indolactam F;
(xv) $N^1$,14-O-bis(3'-phenylpropyl)-(9S,12S)-indolactam A;
(xvi) $N^1$,14-O-di(cyclohexylmethyl)-(9S,12S)-indolactam V; and
(xvii) $N^1$,14-O-bis(tetrahydro-3'-furanmethyl)-(9S,12S)-indolactam V.

EXAMPLE 10

$N^1$-(2',4'-Difluorobenzyl)-(9S,12S)-indolactam V

To a suspension of 34 mg (0.84 mmol) of 60% sodium hydride in 0.5 mL of N,N-dimethylformamide at 0° C. was added 140 mg (330 µmol) of (−)-14-O-tert-butyldimethylsilylindolactam V. After 10 min, 107 mg (535 µmmol) of α-bromo-2,4-difluorotoluene in 0.5 mL N,N-dimethylformamide was added. After stirring at 0° C., the N,N-dimethylformamide was removed in vacuo and the residue was partitioned between methylene chloride and water. The organic layer was separated, dried over sodium sulfate and concentrated in vacuo. The residue was dissolved in 10 mL dry tetrahydrofuran and treated with 1 mL (1 mmol) of 1M tetrabutylammonium fluoride in tetrahydrofuran. After stirring for 10 min, the mixture was concentrated in vacuo. The residue was partitioned between brine and methylene chloride. The organic layer was dried over sodium sulfate and concentrated in vacuo. This residue was subjected to preparative liquid chromatography {0.5×1' column; silica; hexane/ethyl acetate (40:60)} to afford 103.7 mg (242 µmol; 73.5% yield) of $N^1$-(2',4'-difluorobenzyl)-(9S,12S)-indolactam V which was characterized by its NMR spectrum.

EXAMPLE 11

$N^1$-(2,4-Difluorobenzyl)-14-O-methyl-(9S,12S)-indolactam V

A solution of 25 mg (58 µmol) of $N^1$-(2,4-difluorobenzyl)-(9S,12S)-indolactam V in 300 µL of dry N,N-dimethylformamide was added to 17 mg (0.4 mmol) of 60% sodium hydride in a 5 mL round-bottom flask maintained at 0° C. under nitrogen. After 10 minutes 32 mg (170 µmol) of methyl p-toluenesulfonate in 100 µL of N,N-dimethylformamide was added. After another 40 minutes the mixture was allowed to warm to room temperature and about three hours later was diluted with methylene chloride and water. The organic layer was separated, filtered through layers of sodium chloride and sodium sulfate and concentrated in vacuo. The residue was subjected to preparative liquid chromatography {⅜×1' column; silica; hexane/ethyl acetate (75:25)} to afford 16.2 mg (36.7 µmol; 63% yield) of N[1]-(2,4-difluorobenzyl)-14-O-methyl-(9S,12S)-indolactam V which was characterized by its NMR spectrum.

EXAMPLE 12

In a similar manner the following compounds are prepared:
(i) N[1']-ethyl-14-O-prenyl-(9R,12R)-indolactam V;
(ii) N[1]-octyl-14-O-benzyl-(9R,12S)-indolactam V;
(iii) N[1]-prenyl-14-O-ethyl-(9S,12S)-indolactam F;
(iv) N[1]-(2'-trans-heptenyl)-14-O-methyl-(9S,12S)-indolactam V;
(v) N[1]-propargyl-14-O-(tetrahydro-3 '-furanylmethyl)-(9S,12S)-indolactam V;
(vi) N[1]-(2'-hexynyl)-14-O-cyclohexylmethyl-(9S,12S)-indolactam V;
(vii) N[1]-cinnamyl- 1 4-O-(3'-phenylpropyl)-(9S, 12S)-indolactam V;
(viii) N[1]-benzyl-14-O-(2'-pyridinemethyl)-(9S,12S)-indolactam V; and
(ix) 14-O-allyl-1,7-trimethyleneindolactam V.

EXAMPLE 13

14-O-Tri(isopropyl)silyl-(9S,12S)-indolactam V

To a stirred solution of 377 mg of (−)-indolactam V and 240 mg of imidazole in 2 mL of N,N-dimethylformamide was added 477 mg of tri(isopropyl)silyl chloride in about 100 µL of N,N-dimethylformamide. After 30 minutes the solvent was removed in vacuo. The residue was subjected to preparative liquid chromatography {1×1' column; silica; methylene chloride/ethyl acetate (98:2)} to afford 396 mg of 14-O-tri(isopropyl)silyl-(9S,12S)-indolactam V which was characterized by its NMR spectrum.

EXAMPLE 14

N[1]-(t-Butoxycarbonyl)-(9S,12S)-indolactam V

To a suspension of 29 mg of 60% sodium hydride in 2 mL of N,N-dimethylformamide at 0° C. was added 99 mg of 14-O-tri(isopropyl)silyl-(9S,12S)-indolactam V. After 15 min, about 40 mg of t-butylcarbonate in 100 µL N,N-dimethylformamide was added. After stirring at room temperature overnight the mixture was partitioned between ethyl acetate and phosphate buffer (pH 4). The organic layer was separated, dried over sodium sulfate and concentrated in vacuo. The residue was dissolved in 5 mL dry tetrahydrofuran and treated with 2 mL of 1 M tetrabutylammonium fluoride in tetrahydrofuran. After stirring for 3 hours, the mixture was concentrated in vacuo. The residue was partitioned between ethyl acetate and phosphate buffer (pH 8). The organic layer was dried over sodium sulfate and concentrated in vacuo. This residue was subjected to preparative liquid chromatography {0.5×1' column; silica; hexane/ethyl acetate (47:53)} to afford 61 mg of N[1]-(t-butoxycarbonyl)-(9S,12S)-indolactam V which was characterized by its NMR spectrum.

EXAMPLE 15

Protein Kinase C Binding Effects

Recombinant protein kinase Cα, β₁, γ, ε, η, θ and µ were obtained as crude cell preparations as follows. The protein kinase C isotypes were expressed in Sf9 or Sf158 insect cells using recombinant baculoviruses as described (Patel and Stabel, 1989; Stabel, Schaap and Parker, 1991; Johannes et al., 1994). In the case of the θ isotype, human protein kinase Cθ was cloned in the plasmid vector pFlag-Mac and the protein expressed in E. coli strain DH5. Successful full-length expression of each isotype was confirmed by immunoblotting of infected insect cell or E. coli lysates with isotype-specific antibodies (Marais and Parker, 1989) as described (Liyange et al, 1992). Sf9 or Sf158 cells were infected with recombinant baculovirus isolates containing the specified protein kinase C isotype cDNAs (Parker et al, 1986; Coussens et al, 1986) or a non-protein kinase C-related adenovirus E1 a gene (Patel and Jones, 1990). After 3 days infected and uninfected control cells were collected by centrifugation at 600 RCF for 15 min and frozen. To obtain crude insect cell-expressed recombinant protein kinase C isotypes for binding experiments, frozen infected insect cells, obtained and harvested as above, were thawed and suspended at 0.5–3×10⁶ cells/mL by vortexing vigorously at 0° C. in 50 mM Tris-HCl, pH 7.4, containing 1 mM $CaCl_2$, 100 µg/mL phosphatidylserine and 2 mM phenylmethylsulfonyl fluoride. After removal of samples for protein determination (Bradford, 1976) 4 mg/mL bovine gamma globulin and 10% glycerol (final concentrations) were added and the suspensions were re-frozen in aliquots until use.

EXAMPLE 16

[³H]PDBu Receptor Assays

The assay was carried out in 0.5 mL polypropylene centrifuge tubes. The final volume of 0.25 mL contained 50 mM Tris·HCl, pH 7.4, 1 mM $CaCl_2$, 4 mg/mL bovine gamma globulin, 1.25–50 ug mouse brain cytosolic or crude insect cell protein, [³H]PDBu (18.5–20.0 Ci/mmole; each lot was purified by HPLC before use) at concentrations indicated in the figures, 1% DMSO, 100 µg/mL phosphatidylserine and other ligands as specified. Additions were made at 0° C.; the tubes were vortexed, incubated at 37° C. for 15 min, placed on ice, treated with 150 µL 37% polyethylene glycol 8000 in 50 mM Tris·HCl/pH 7.4, held on ice for 10 min and centrifuged at 13,000 RCF for 30 min at 4° C. in the Sorvall SH-MT rotor. Specific and nonspecific binding values were then determined as described (Driedger and Blumberg, 1980b). Counting was done in 2 mL Aquasol 2 at efficiencies of 30–35%. Apparent $K_i$ values for test compounds of this invention were calculated (Cheng and Prusoff, 1973) from the equation $K_i=I_{50}/(1+L/K_d)$, where L is the concentration of free [³H]PDBu, $K_d$ is the measured dissociation constant for PDBu on each receptor source, and $I_{50}$ is the concentration of competing ligand producing a 50% decrease in binding of the [³H]PDBu.

EXAMPLE 17

Protein Kinase C Isotype Selectivity of N[1],14-O-digeranyl-(9S,12S)-indolactam V Using the methods set forth above in Examples 15 and 16, the Ki for N[1],14-O-digeranyl-(9S,12S)-indolactam V was found to be weak for protein kinase C's α, β₁ and γ, showing Ki's of 5.9, 3.8 and 6.5 µM, respectively, whereas it was much more potent for protein kinase C's δ, ε, η, θ and µ, for which it showed Ki's of 0.9, 0.3, 0.5, 0.9 and 0.5 µM, respectively. By similar procedures the protein kinase C isotype selectivities of the following compounds are shown:
(i) N[1],14-O-dioctyl-(9S,12S)-indolactam V;
(ii) N[1],14-O-bis(2'-trans-heptenyl)-(9S,12S)-indolactam V;

(iii) $N^1$,14-O-dipropargyl-(9S,12S)-indolactam V;
(iv) $N^1$,14-O-bis(4'-tert-butylbenzyl)-(9S,12S)-indolactam V;
(v) $N^1$,14-O-dicinnamyl-(9S,12S)-indolactam V;
(vi) $N^1$,14-O-diethyl-(9S,12S)-indolactam V;
(vii) $N^1$-octyl-(9S,12S)-indolactam V;
(viii) $N^1$-(2'-trans-heptenyl)-(9S,12S)-indolactam V;
(ix) $N^1$-geranyl-(9S,12S)-indolactam V;
(x) $N^1$-propargyl-(9S,12S)-indolactam V;
(xi) $N^1$-prenyl-(9S,12S)-indolactam V;
(xii) $N^1$-(4'-tert-butylbenzyl)-(9S,12S)-indolactam V;
(xiii) $N^1$-cinnamyl-(9S,12S)-indolactam V;
(xiv) $N^1$-(2'-hexynyl)-(9S,12S)-indolactam V;
(xv) $N^1$-benzyl-(9S,12S)-indolactam V;
(xvi) $N^1$-(2',4'-difluorobenzyl)-(9S,12S)-indolactam V; and
(xvii) $N^1$-(2',4'-difluorobenzyl)-14-O-methyl-(9S,12S)-indolactam V.

EXAMPLE 18

Anti-inflammatory Activity

Method: A stock solution of 300 pmoles of the standard inflammatory compound phorbol 12-myristate 13-acetate per 5 μL acetone was prepared. This solution was used to prepare ten-fold dilutions of $N^1$,14-O-digeranyl-(9S,12S)-indolactam V, prepared as in Example 8, covering concentrations of the latter ranging from 3,500 to 350,000 pmoles per 5 μL. These solutions were used to demonstrate the anti-inflammatory activity of the latter compound by application of 5 μL to the insides of the right ears of mice, followed by the observation of ear inflammation/erythema at intervals from 1 to 48 hours after application. Inhibition of the phorbol 12-myristate 13-acetate induced inflammation was observed at the medium and high concentrations of the inhibitor, with inhibition persisting for the duration of the experiment at the highest concentration.

In a like manner, the anti-inflammatory activities of the following compounds are demonstrated; lower doses produce shorter periods of inflammation/erythema and higher doses produce longer periods of, and in many cases complete, inhibition during the entire assay period:

(i) $N^1$,14-O-dioctyl-(9S,12S)-indolactam V;
(ii) $N^1$-(2',4'-difluorobenzyl)-14-O-methyl-(9S,12S)-indolactam V;
(iii) $N^1$-cinnamyl-(9S,12S)-indolactam V;
(iv) $N^1$,14-O-bis(4'-tert-butylbenzyl)-(9S,12S)-indolactam V;
(v) $N^1$,14-O-dicinnamyl-(9S,12S)-indolactam V;
(vi) $N^1$,14-O-diethyl-(9S,12S)-indolactam V;
(vii) $N^1$-octyl-(9S,12S)-indolactam V;
(viii) $N^1$-(2'-trans-heptenyl)-(9S,12S)-indolactam V;
(ix) $N^1$-geranyl-(9S,12S)-indolactam V;
(x) $N^1$-propargyl-(9S,12S)-indolactam V;
(xi) $N^1$-prenyl-(9S,12S)-indolactam V;
(xii) $N^1$-(4'-tert-butylbenzyl)-(9S,12S)-indolactam V;
(xiii) $N^1$-(2'-hexynyl)-(9S,12S)-indolactam V;
(xiv) $N^1$-benzyl-(9S,12S)-indolactam V; and
(xv) $N^1$-(2',4'-difluorobenzyl)-(9S,12S)-indolactam V.

EXAMPLE 19

Gelatin Capsules

Gelatin capsules containing the following ingredients are prepared:

| | |
|---|---|
| $N^1$-(2'-trans-heptenyl)-14-O-allyl-(9S,12S)-indolactam V | 125 mg |
| lactose | 300 mg |
| talc | 15 mg |

The finely powdered ingredients are blended together. The mixture is used to fill hard shell two-piece gelatin capsules of a suitable size at a net fill weight of 440 mg.

EXAMPLE 20

Injectable Solution

A suspension (1.0 mL) suitable for intramuscular injection is prepared from the following ingredients:

| | |
|---|---|
| $N^1$,14-O-dicinnamyl-(9S,12S)-indolactam V | 20 mg |
| polyethylene glycol 3350 | 29 mg |
| polysorbate 80 | 2 mg |
| monobasic sodium phosphate | 6.8 mg |
| dibasic sodium phosphate | 1.4 mg |
| benzyl alcohol | 9 mg |
| water for injection to make | 1.0 ml |

The materials are mixed, homogenized and filled into 1 ml ampuls which are sealed.

EXAMPLE 21

Topical Gel

An illustrative composition for a topical gel is the following:

| | |
|---|---|
| $N^1$,14-O-digeranyl-(9S,12S)-indolactam V | 20 mg |
| hydroxypropylcellulose | 60 mg |
| ethyl alcohol | 920 mg |

The materials are mixed, homogenized and filled into containers each holding 1 gram of gel.

EXAMPLE 22

Topical Solution

An illustrative composition for a topical solution is the following:

| | |
|---|---|
| $N^1$-(2',4'-difluorobenzyl)-14-O-methyl-(9S,12S)-indolactam V | 20 mg |
| propylene glycol | 300 mg |
| citric acid | 20 mg |
| SD alcohol 40-2 to make | 1.0 mL |

The materials are mixed, homogenized and filled into squeezable plastic containers each holding 1 milliliter of solution.

EXAMPLE 23

Protein Kinase C Isotype Selectivity of 14-O-alkyl-(9S,12S)-indolactam V

The 14-O-alkylindolactams listed below were prepared according to the method of Irie and Koshimizu, op. cit.

These compounds were also evaluated by the method described in Example 17. Each of the compounds listed below exhibited essentially no binding to each of the protein kinase C isotypes, except possibly at very high concentrations.

The compounds tested were:
(i) 14-O-methyl-(9S,12S)-indolactam V;
(ii) 14-O-ethyl-(9S,12S)-indolactam V; and
(iii) 14-O-hexyl-(9S,12S)-indolactam V.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A compound of the formula:

wherein $P_I$ is a moiety of the formula:

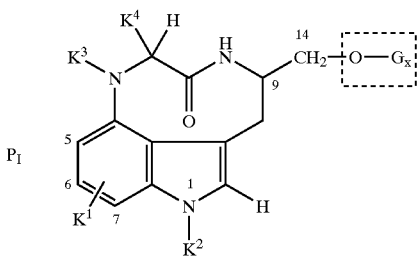

in the form of an individual isomer, an isomer mixture, a racemate or optical antipode, or a pharmaceutically acceptable salt thereof;

wherein $K^1$ represents 1–3 substituents located independently at any of carbons 5, 6 and 7, which substituents are selected from the group consisting of hydrogen, halogen and a straight chain or branched chain, cyclic or acyclic, saturated or unsaturated or aromatic carbon- and/or heteroatom-containing moiety which moieties, taken together, contain not more than 40 carbon atoms, not more than 24 halogen atoms and not more than 9 heteroatoms selected from the group consisting of oxygen, nitrogen, silicon, phosphorus, and sulfur, the moieties being optionally connected to one another, to $K^3$ and/or to $K^2$ to form 1–3 additional carbocyclic or heterocyclic rings;

wherein $K^2$ is a straight chain or branched chain, cyclic or acyclic, saturated or unsaturated or aromatic carbon- and/or heteroatom-containing moiety which is bound to $N^1$ via a carbon atom of the moiety and which contains 1–40 carbon atoms, not more than 20 halogen atoms and not more than 8 heteroatoms selected from the group consisting of oxygen, nitrogen, silicon, phosphorus and sulfur, said moiety being optionally connected to $K^1$ to form an additional carbocyclic or heterocyclic ring;

wherein $K^3$ is hydrogen or a straight chain or branched chain, cyclic or acyclic, saturated or unsaturated or aromatic carbon- and/or heteroatom-containing moiety containing not more than 30 carbon atoms, not more than 24 halogen atoms and not more than 8 heteroatoms selected from the group consisting of oxygen, nitrogen, silicon, phosphorus and sulfur, said moiety being optionally connected to either $K^4$ or $K^1$ to form an additional ring;

wherein $K^4$ is hydrogen or a straight chain or branched chain, cyclic or acyclic, saturated or unsaturated or aromatic carbon- and/or heteroatom-containing moiety containing not more than 20 carbon atoms, not more than 24 halogen atoms and not more than 9 heteroatoms selected from the group consisting of oxygen, nitrogen, silicon, phosphorus and sulfur, said moiety being optionally connected to $K^3$ to form an additional ring; and wherein $G_x$ is bound to the oxygen atom attached to carbon 14 of $P_I$ and comprises a moiety selected from the group consisting of substituted or unsubstituted, straight or branched, acyclic or cyclic alkyls, alkenyls, alkynyls, aryls and aralkyls containing not more than 30 carbon atoms, not more than 15 halogen atoms and not more than 8 heteroatoms selected from the group consisting of oxygen, nitrogen, silicon, phosphorus and sulfur; provided that carbon 14 of $P_I$, the oxygen atom and the carbon atom of $G_x$ which is attached to 14-O form an ether linkage; and provided that $P_I$—O—$G_x$ may not be $N^1$,14-O-dimethyl-(9S,12S)-indolactam V.

2. A compound of claim 1 selected from the group consisting of:
(i) $N^1$,14-O-diethyl-(9S,12S)-indolactam V;
(ii) $N^1$,14-O-bis(4'-tert-butylbenzyl)-(9S,12S)-indolactam V;
(iii) $N^1$-ethyl-14-O-prenyl-(9R,12R)-indolactam V;
(iv) $N^1$-prenyl-14-O-ethyl-(9S,12S)-indolactam F;
(v) $N^1$-propargyl-14-O-(tetrahydro-3'-furanmethyl)-(9S,12S)-indolactam V;
(vi) 14-O-allyl-1,7-trimethyleneindolactam V;
(vii) $N^1$,14-O-dipropargyl-(9S,12S)-indolactam V;
(viii) $N^1$,14-O-bis(2'-trans-heptenyl)-(9R,12R)-indolactam V;
(ix) $N^1$,14-O-bis(2'-trans-heptenyl)-(9R)-indolactam G;
(x) rac-$N^1$,14-O-digeranyl-13-desmethyl-$N^{13}$-ethylindolactam G;
(xi) $N^1$,14-O-digeranyl-(9S,12S)-indolactam L;
(xii) $N^1$,14-O-bis(2'-pyridinemethyl)-(9S,12S)-indolactam F;
(xiii) $N^1$,14-O-bis(3'-phenylpropyl)-(9S,12S)-indolactam A; and
(xiv) $N^1$,14-O-bis(3'-nitrobenzyl)-(9S,12R)-indolactam V.

3. A compound of claim 1 wherein O—$G_x$ is methoxy.

4. A compound of claim 1 wherein $K^2$ contains 4–30 carbon atoms, 0–15 halogen atoms and 0–4 heteroatoms selected from the group consisting of oxygen, nitrogen, sulfur, phosphorus and silicon; and wherein $G_x$ contains 1–10 carbon atoms, 0–5 halogen atoms and 0–3 heteroatoms selected from the group consisting of oxygen, nitrogen, sulfur, phosphorus and silicon.

5. A compound of claim 1 wherein $K^3$ is methyl and $K^4$ is isopropyl forming $P_V$

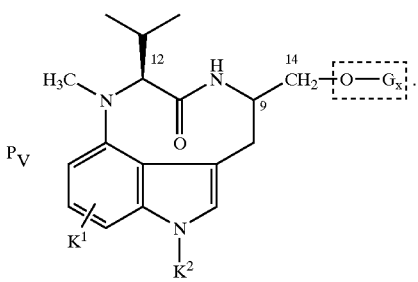

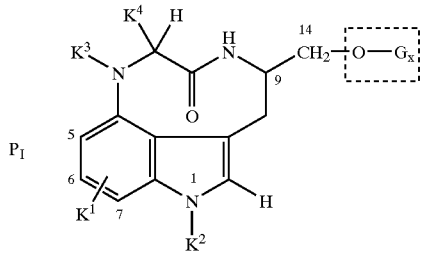

6. A compound of claim 5 wherein O—$G_x$ is methoxy.

7. A compound of claim 6 selected from the group consisting of:
   (i) $N^1$-(2',4'-difluorobenzyl)-14-O-methyl-(9S,12S)-indolactam V; and
   (ii) $N^1$-(2'-trans-heptenyl)-14-O-methyl-(9S,12S)-indolactam V.

8. A compound of claim 5 wherein $K^2$ contains 4–30 carbon atoms, 0–15 halogen atoms and 0–4 heteroatoms selected from the group consisting of oxygen, nitrogen, sulfur, phosphorus and silicon; and wherein $G_x$ contains 1–10 carbon atoms, 0–5 halogen atoms and 0–3 heteroatoms selected from the group consisting of oxygen, nitrogen, sulfur, phosphorus and silicon.

9. A compound of claim 8 selected from the group consisting of:
   (i) $N^1$,14-O-dioctyl-(9S,12S)-indolactam V;
   (ii) $N^1$,14-O-digeranyl-(9S,1 2S)-indolactam V;
   (iii) $N^1$,14-O-dicinnamyl-(9S,12S)-indolactam V;
   (iv) $N^1$-octyl-14-O-benzyl-(9R,12S)-indolactam V;
   (v) $N^1$-(2'-hexynyl)-14-O-cyclohexylmethyl-(9S,12S)-indolactam V;
   (vi) $N^1$-cinnamyl-14-O-(3'phenylpropyl)-(9S,12S)-indolactam V;
   (vii) $N^1$-benzyl-14-O-(2'-pyridinemethyl)-(9S,12S)-indolactam V;
   (viii) $N^1$,14-O-di(t-butylethyl)-(9S,12S)-indolactam V;
   (ix) $N^1$,14-O-diprenyl-(9S,12S)-indolactam V;
   (x) $N^1$,14-O-bis(2'-trans-heptenyl)-(9S,12S)-indolactam V;
   (xi) $N^1$,14-O-bis(2'-hexynyl)-(9S,12S)-indolactam V;
   (xii) $N^1$,14-O-dibenzyl-(9S,12S)-indolactam V;
   (xiii) $N^1$,14-O-bis(2',4'-difluorobenzyl)-(9S,12S)-indolactam V;
   (xiv) $N^1$,14-O-di(cyclohexylmethyl)-(9S,12S)-indolactam V;
   (xv) $N^1$,14-O-bis(tetrahydro-3'-furanylmethyl)-(9S,12S)-indolactam V; and
   (xvi) $N^1$,14-O-digeranyl-(9R,12S)-indolactam V.

10. A composition, comprising:
   a physiologically acceptable pharmaceutical carrier; and
   a compound, in a quantity of between about 0.001 and 1000 mg per unit dosage, of the formula:

$$P_I\text{—O—}G_x$$

wherein $P_I$ is a moiety of the formula:

in the form of an individual isomer, an isomer mixture, a racemate or optical antipode, or a pharmaceutically acceptable salt thereof;
wherein $K^1$ represents 1–3 substituents located independently at any of carbons 5, 6 and 7, which substituents are selected from the group consisting of hydrogen, halogen and a straight chain or branched chain, cyclic or acyclic, saturated or unsaturated or aromatic carbon- and/or heteroatom-containing moiety which moieties, taken together, contain not more than 40 carbon atoms, not more than 24 halogen atoms and not more than 9 heteroatoms selected from the group consisting of oxygen, nitrogen, silicon, phosphorus, and sulfur, the moieties being optionally connected to one another, to $K^3$ and/or to $K^2$ to form 1–3 additional carbocyclic or heterocyclic rings;
wherein $K^2$ is a straight chain or branched chain, cyclic or acyclic, saturated or unsaturated or aromatic carbon- and/or heteroatom-containing moiety which is bound to $N^1$ via a carbon atom of the moiety and which contains 1–40 carbon atoms, not more than 20 halogen atoms and not more than 8 heteroatoms selected from the group consisting of oxygen, nitrogen, silicon, phosphorus and sulfur, said moiety being optionally connected to $K^1$ to form an additional carbocyclic or heterocyclic ring;
wherein $K^3$ is hydrogen or a straight chain or branched chain, cyclic or acyclic, saturated or unsaturated or aromatic carbon- and/or heteroatom-containing moiety containing not more than 30 carbon atoms, not more than 24 halogen atoms and not more than 8 heteroatoms selected from the group consisting of oxygen, nitrogen, silicon, phosphorus and sulfur, said moiety being optionally connected to either $K^4$ or $K^1$ to form an additional ring;
wherein $K^4$ is hydrogen or a straight chain or branched chain, cyclic or acyclic, saturated or unsaturated or aromatic carbon- and/or heteroatom-containing moiety containing not more than 20 carbon atoms, not more than 24 halogen atoms and not more than 9 heteroatoms selected from the group consisting of oxygen, nitrogen, silicon, phosphorus and sulfur, said moiety being optionally connected to $K^3$ to form an additional ring; and
wherein $G_x$ is bound to the oxygen atom attached to carbon 14 of $P_I$ and comprises a moiety selected from the group consisting of substituted or unsubstituted, straight or branched, acyclic or cyclic alkyls, alkenyls, alkynyls, aryls and aralkyls containing not more than 30 carbon atoms, not more than 15 halogen atoms and not more than 8 heteroatoms selected from the group consisting of oxygen, nitrogen, silicon, phosphorus and sulfur; provided that carbon 14 of $P_I$, the oxygen atom and the carbon atom of $G_x$ which is attached to 14-O form an ether linkage.

11. A composition of claim 10 wherein O—$G_x$ is methoxy.

12. A composition of claim 10 wherein $K^2$ contains 4–30 carbon atoms, 0–15 halogen atoms and 0–4 heteroatoms selected from the group consisting of oxygen, nitrogen, sulfur, phosphorus and silicon; and wherein $G_x$ contains 1–10 carbon atoms, 0–5 halogen atoms and 0–3 heteroatoms selected from the group consisting of oxygen, nitrogen, sulfur, phosphorus and silicon.

13. A composition of claim 10 wherein $K^3$ is methyl and $K^4$ is isopropyl forming $P_V$:

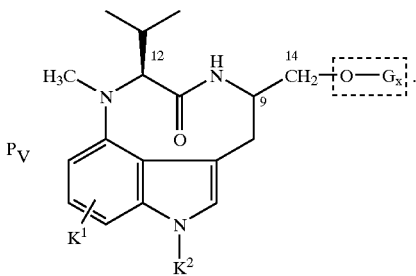

14. A composition of claim 13 wherein O—$G_x$ is methoxy.

15. A composition of claim 14 wherein the compound is selected from the group consisting of:

(i) $N^1$-(2',4'-difluorobenzyl)-14-O-methyl-(9S,12S)-indolactam V; and (ii) $N^1$-(2'-trans-heptenyl)-14-O-methyl-(9S,12S)-indolactam V.

16. A composition of claim 11 wherein $K^2$ contains 4–30 carbon atoms, 0–15 halogen atoms and 0–4 heteroatoms selected from the group consisting of oxygen, nitrogen, sulfur, phosphorus and silicon; and wherein $G_x$ contains 1–10 carbon atoms, 0–5 halogen atoms and 0–3 heteroatoms selected from the group consisting of oxygen, nitrogen, sulfur, phosphorus and silicon.

17. A composition of claim 16 wherein the compound is selected from the group consisting of:

(i) $N^1$,14-O-dioctyl-(9S,12S)-indolactam V;

(ii) $N^1$,14-O-digeranyl-(9S,12S)-indolactam V; and (iii) $N^1$,14-O-dicinnamyl-(9S,12S)-indolactam V.

18. A method of modulating protein kinase C activity comprising the step of contacting protein kinase C, in vitro or in vivo, with a protein kinase C-modulating amount of a compound of claim 1.

19. A method of modulating protein kinase C activity comprising the step of contacting protein kinase C, in vitro or in vivo, with a protein kinase C-modulating amount of a composition of claim 10.

20. A method of treating inflammation in a mammal in need of anti-inflammatory or anti-psoriatic treatment comprising the step of administering to said mammal a composition of claim 10.

* * * * *